Figure 1A:
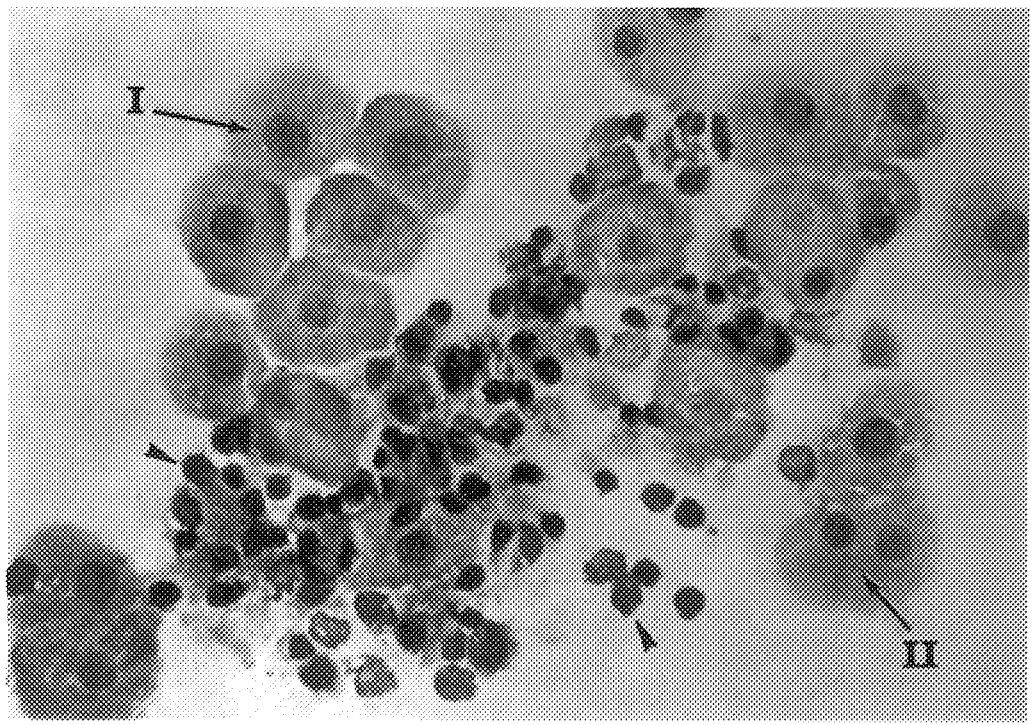

US005849588A

United States Patent [19]
Naughton et al.

[11] Patent Number: 5,849,588
[45] Date of Patent: Dec. 15, 1998

[54] METHODS OF USE OF A THREE-DIMENSIONAL LIVER CELL AND TISSUE CULTURE SYSTEM

[75] Inventors: Brian A. Naughton; Gail K. Naughton, both of El Cajon, Calif.

[73] Assignee: Advanced Tissue Sciences, Inc., La Jolla, Calif.

[21] Appl. No.: 690,955

[22] Filed: Aug. 1, 1996

Related U.S. Application Data

[62] Division of Ser. No. 445,441, May 31, 1995, Pat. No. 5,624,840, which is a division of Ser. No. 241,259, May 11, 1994, Pat. No. 5,510,254, which is a continuation-in-part of Ser. No. 131,361, Oct. 4, 1993, Pat. No. 5,443,950, which is a division of Ser. No. 575,518, Aug. 30, 1990, Pat. No. 5,266,480, which is a division of Ser. No. 402,104, Sep. 1, 1989, Pat. No. 5,032,508, which is a continuation-in-part of Ser. No. 242,096, Sep. 8, 1988, Pat. No. 4,963,489, which is a continuation-in-part of Ser. No. 38,110, Apr. 14, 1987, abandoned, which is a continuation-in-part of Ser. No. 36,154, Apr. 3, 1987, Pat. No. 4,721,096, which is a continuation of Ser. No. 853,569, Apr. 18, 1986, abandoned.

[51] Int. Cl.⁶ .............. C12N 5/00; C12M 3/00; A61K 2/00
[52] U.S. Cl. ............... 435/373; 435/395; 435/396; 435/397; 435/398; 435/399; 435/402
[58] Field of Search .................. 435/240, 243, 435/240.1, 240.2, 240.23, 284.1, 395, 396, 397, 398, 399, 400, 402, 29, 347, 373

[56] References Cited

U.S. PATENT DOCUMENTS

| | | | |
|---|---|---|---|
| 3,997,396 | 12/1976 | Delente | 435/240.242 |
| 4,016,036 | 4/1977 | Green et al. | 435/240.23 |
| 4,024,020 | 5/1977 | Weiss et al. | 435/240.243 |
| 4,087,327 | 5/1978 | Feder et al. | 435/240.241 |
| 4,107,937 | 8/1978 | Chmiel | 62/64 |
| 4,117,881 | 10/1978 | Williams et al. | 165/2 |
| 4,135,975 | 1/1979 | Lichtman et al. | 435/240.73 |
| 4,144,126 | 3/1979 | Burbridge | 435/240.23 |
| 4,228,243 | 10/1980 | Iizuka | 435/285 |
| 4,280,954 | 7/1981 | Yannas | 530/356 |
| 4,299,819 | 11/1981 | Eisinger | 435/41 |
| 4,342,828 | 8/1982 | Takaku et al. | 435/41 |
| 4,458,678 | 7/1984 | Yannas et al. | 602/48 |
| 4,481,946 | 11/1984 | Altshuler et al. | 606/4 |
| 4,485,096 | 11/1984 | Bell | 424/532 |
| 4,485,097 | 11/1984 | Bell | 424/549 |
| 4,486,188 | 12/1984 | Altshuler et al. | 604/4 |
| 4,489,710 | 12/1984 | Spitler | 128/898 |
| 4,520,821 | 6/1985 | Schmidt et al. | 606/151 |
| 4,539,716 | 9/1985 | Bell | 623/1 |
| 4,546,500 | 10/1985 | Bell | 435/1.1 |
| 4,553,272 | 11/1985 | Mears | 623/1 |
| 4,604,346 | 8/1986 | Bell | 606/132 |
| 4,621,100 | 11/1986 | Lund et al. | 514/573 |
| 4,642,292 | 2/1987 | Reid et al. | 435/240.243 |
| 4,645,669 | 2/1987 | Reid | 424/520 |
| 4,703,108 | 10/1987 | Silver | 530/356 |
| 4,835,102 | 5/1989 | Bell | 435/29 |

FOREIGN PATENT DOCUMENTS

| | | |
|---|---|---|
| 0075904 | 4/1983 | European Pat. Off. . |
| 85109336 | 1/1986 | European Pat. Off. . |
| 85303844 | 12/1986 | European Pat. Off. . |
| 86306544 | 3/1987 | European Pat. Off. . |
| 0081781 | 5/1983 | Japan . |
| 60-123884 | 12/1985 | Japan . |
| WO83/04177 | 12/1983 | WIPO . |
| WO 88/03785 | 6/1988 | WIPO . |

OTHER PUBLICATIONS

Freshney, "Culture Of Animal Cells, A Manual Of Basic Technique" 1983, Alan R. Liss, Inc. N.Y.
Lydersen, "Layer Scale Cell Culture Technology" 1987, Hansen Publishers, Munich, Vernon, New York.
Thilly, "Mammalian Cell Technology," 1986, Butterworths, Boston, London, Durban, Singapore, Sydney, Toronto, Wellington.
Sarber, et al., 1981, Mechanisms of Aging and Development, 17:107–117.
Nusgens et al., 1984, Collagen Rel. Res. 4:351–364.
Leighton, J., 1951, J:N.C.I. 12:545–561.
Schneider, H. et al., 1963, Exp. Cell Res. 30:449–459.
Kruse, P. et al., 1965, J.Cell Biol. 27:273–279.
Leighton, J. et al., 1967, Science 155:1259–1261.
Leighton, J. et al., 1968, Cancer Res. 28:286–296.
Elsdale et al., 1972, J. Cell Biol. 54:626–637.
Ansevin, K. et al., 1973, In Vitro 8:483–488.
Sobour, O. et al., 1975, J. Neurosurg 43:742–749.
Douglas, W.H. et al., 1976, In Vitro 12:373–381.
Ebendal, E., 1976, Exp. Cell Res. 98:159–169.
Emerman, J., et al., 1977, Proc. Natl. Acad. Sci. U.S.A. 74:4466–4470.
Bell, E., et al., 1979, PNAS 76;1274–1278.
Lindsay, R., 1979, Nature 282:80–82.
Reid, L. et al., 1979, 58:263–278.
Yang, J. et al., 1979, Proc. Natl. Acad. Sci. U.S.A. 76:3401–3405.
Douglas, W. et al., 1980, In Vitro 16:306–312.
Folkman, J. et al., Nature 288:551–555.

(List continued on next page.)

Primary Examiner—Sandra E. Saucier
Attorney, Agent, or Firm—Pennie & Edmonds LLP

[57] ABSTRACT

The present invention relates to a three-dimensional cell and tissue culture system. In particular, it relates to this culture system for the long term culture of liver cells and tissues in vitro in an environment that more closely approximates that found in vivo. The culture system described herein provides for proliferation and appropriate liver cell maturation to form structures analogous to tissue counterparts in vivo. The resulting liver tissues survive for prolonged periods, perform liver-specific functions, and maintain hepatic tissue architecture following in vivo implantation.

The liver cultures have a variety of applications ranging from transplantation or implantation in vivo, to screening cytotoxic compounds and pharmaceutical compounds in vitro, to the production of biologically active molecules in "bioreactors" and to the construction of extracorporeal liver assist device.

20 Claims, 8 Drawing Sheets

OTHER PUBLICATIONS

Vlodavsky, D. et al., 1980, Cell 19:607–616.
Yang, J. et al., 1980, PNAS 77:2088–2092.
Yang, J. et al., 1981, Cancer Res. 41:1021–1027.
Thuroff, et al., 1983, Urology 21:155–158.
Daniels, E. and Moore, 1969, Anat. Rec. 163:174.
Daniels, E., 1975, Anat. Rec. 181:341.
Dexter, T. M. et al., 1976, in "Methods in Cell Biology," editor D. M. Prescott, pp. 387–405, Academic Press, N.Y.
Dexter, T. M. et al., 1976, J. Cell. Physiol. 91:335–344.
Blackburn, M. et al., 1977, Br. J. Haematology 37:337.
Dexter, T. M., 1979, Acta Haomat. 62:299–305.
Daniels, E., 1978, Anat. Roc. 190:376.
Moore, M. A. S. et al., 1979, Blood Cells 5:297–311.
Reimann, J. et al., 1979, Exp. Hematol. 7:52–58.
Daniels, E., 1980, Exp. Hematol. 8:157–165.
Gartner, S. et al., 1980, Proc. Natl. Acad. Sci. 77:4756–4759.
Hocking, W. G. et al., 1980, in "Biology of Bone Marrow Transplantation", edited by R. B. Gale, et al., pp. 431–442, Academic Press, N.Y.
Daniels, 1981, Exp. Hematol. 9:697–710.
Daniels, E., 1981, Anat. Rec. 199:63A.
Coulombel et al., 1983, Blood 62:291–297.
Daniels, E., 1983, Res: Journal of Recticuloendothelial Society 33:457–465.
Dexter, T. et al., 1984, in "Long–Term Bone Marrow" editor Wright et al., pp. 57–96, Alan R. Liss, Inc., N.Y.
Greenberger, J. S., 1984, in "Long–Term Bone Marrow Culture", editor D. Wright, pp. 119–131, Alan R. Liss, N.Y.
Phillips, R.A., 1984, in "Long–Term Bone Marrow Culture", editor D. Wright, pp. 309–321, Alan R. Liss, Inc., N.Y.
Chang, J., et al., 1986, The Lancet, pp. 294–295.
Brockbank, K.G.M., et al., 1986, Exp. Homatol. 14:386–394.
McMillen, et al., 1986, J. Surg. Res. 40:193–197.
Naughton et al., 1986, Blood 68:149a.
Page et al., 1986, Exp. Homatol. 14:719–723.
Yuen et al., 1986, Exp. Hematol. 14:771–775.
Hunt et al., 1987, Cell, 48:996–1007.
Ronnick et al., 1987, Blood 69:682–691.
Whitlock et al., 1987, Cell, 48:1009–1021.
E. Daniels, 1977, Anat. Rec. 187:562.
Gorin, N.C. et al., 1978, Blood 51:2157–265.
Ritz et al, 1982, The Lancet, Jul. 10, 1982, pp. 60–63.
Van De Ouweland, F. et al., 1982, Cryobiology 19:292–298.
Parkman, 1986, Science 232:1373–1378.
Green et al., 1978, Science 200:1385–1388.
Bell, E. et al., 1979, Proc. Natl. Acad. Sci. U.S.A. 76:1274–1278.
Green, H. et al., 1979, Proc. Natl. Acad. Sci. U.S.A. 76:5665–5668.
Yannas, I. et al., 1980, J. Biomedical Res. 14:107–131.
Bell, E. et al., 1981, Science 211:1052–1054.
Yannas et al., 1982, Science 215:174–176.
Bell, E. et al., 1983, J. Invest. Dermatol. $81.2_S$–$10_S$.
Kao, J. et al., 1983, Toxicol. and Appl. Pharmacol. 68:206–217 (1983).
Gallico et al., 1984, N. Engl. J. Med. 311:448–451.
Pittelkow et al., 1986, Mayo Clin. Proc. 61:771–777.
Boyce, J., et al., 1988, Surgery 421–431.
Michalopoulos, G. and Pitot, H., 1975, Fed. Proc. 34:826.
Michalopoulos, G., Sattler, G., O'Connor, L., and Savage, R. and Bonney, R., 1978, Exp.Cell Res. 114:307–315.
Sirica, A., Ricahards, W., Tsukada, Y., Sattler, C., and Pitot, H., 1979, Proc. Natl. Acad. Sci., U.S.A. 76:283–287.
Sirica, A., Hwang, C., Sattler G. and Pitot, H., 1980, Cancer Res. 40:3259–3267.
Latsinik et al., 1981, Biol. Abstr. 74:3841.
Gordon et al., 1983, Int. J. Cell Cloning 1:429–39.
Chailakhyan et al., 1984, Biol. Abstr. vol. 80, abstract 28317.
Old Primrose, "Principles Of Gene Manipulation. An Introduction to Genetic Engineering Chapter" in Studies in Microbiology, vol. 2, Third Edition, 1985, Blackwell Scientific Publication.

ETHOXYFLUORESCEIN ETHYL ESTER → FLUORESCEIN

METHODS OF USE OF A THREE-DIMENSIONAL LIVER CELL AND TISSUE CULTURE SYSTEM

This is a division of application Ser. No. 08/445,441, filed May 31, 1995, U.S. Pat. No. 5,624,840; which is a division of application Ser. No. 08/241,259, filed May 11, 1994, U.S. Pat. No. 5,510,254; which is a continuation-in-part of Ser. No. 08/131,361, filed Oct. 4, 1993, U.S. Pat. No. 5,443,950; which is a division of Ser. No. 07/575,518, filed Aug. 30, 1990, U.S. Pat. No. 5,266,480; which is a division of Ser. No. 07/402,104, filed Sep. 1, 1989, U.S. Pat. No. 5,032,508; which is a continuation-in-part of Ser. No. 07/242,096, filed Sep. 8, 1988, U.S. Pat. No. 4,963,489; which is a continuation-in-part of Ser. No. 07/038,110, filed Apr. 14, 1987, abandoned; which is a continuation-in-part of Ser. No. 07/036,154, filed Apr. 3, 1987, U.S. Pat. No. 4,721,096 which is a continuation of Ser. No. 06/853,569, filed Apr. 18, 1986, abandoned; each of which is incorporated by reference herein in its entirety.

1. INTRODUCTION

The present invention relates to a three-dimensional cell and tissue culture system. In particular, it relates to this culture system for the long term culture of liver cells and tissues in vitro in an environment that more closely approximates that found in vivo. The culture system described herein provides for proliferation and appropriate liver cell maturation to form structures analogous to tissue counterparts in vivo. The resulting liver tissues survive for prolonged periods, perform liver-specific functions, and maintain hepatic tissue architecture following in vivo implantation.

The liver cultures have a variety of applications ranging from transplantation or implantation in vivo, to screening cytotoxic compounds and pharmaceutical compounds in vitro, to the production of biologically active molecules in "bioreactors" and to the construction of extracorporeal liver assist device.

2. BACKGROUND OF THE INVENTION

The liver is a dynamic organ that plays an important role in a variety of physiological processes. The complex functions of the liver include metabolism, storage, excretion, secretion of plasma proteins such as albumin and detoxification of harmful substances by enzymes of the cytochrome P-450 system. In addition, the usually quiescent liver is also capable of remarkable mitotic activities under certain circumstances. The major cell population of the liver is the parenchymal cells (PC), also known as hepatocytes. The liver also contains several other cell types such as endothelial cells, adipocytes, fibroblastic cells and Kupffer cells, collectively referred to as stromal (littoral) cells.

2.1 LIVER CELL CULTURES

In an attempt to study the diverse liver functions and the cell types responsible therefor, in vitro cultures of liver cells have been prepared from humans as well as from experimental animals. Primary cultures of rat hepatocytes have been used extensively to study the effects of potential toxins on enzyme leakage, metabolism, and cellular membranes (Grisham, 1979, Int. Rev. Exp. Pathol. 20:123–210; Acosta and Mitchell, 1981, Biochem. Pharmacol. 30:3225–3230). However, such culture systems have a number of drawbacks, and none have provided for the proliferation of liver PC.

In vitro, adult hepatocytes proliferate for only short time periods, although their ability to produce albumin and display cytochrome P-450 enzyme activity may be prolonged if they are co-cultured with other liver-derived extracellular matrix (ECM) substances or with certain combinations thereof. In liquid culture, the viability of hepatocytes and the ability of these cells to manifest inducible cytochrome P-450 enzyme activity decline as a function of time (Sirica and Pitot, 1980, Pharmacol. Rev. 31:205–228). In addition, cell division usually is limited to the first 24–48 hr of culture (Clayton and Darnell, 1983, Mol. Cell Biol. 3:1552–1561; Chapman et al., 1973, J. Cell Biol. 59:735–747). The viability of adherent hepatocytes in monolayer cultures persists for somewhat longer periods but specialized activity is also lost rapidly (Deschenes et al., 1980, In Vitro 16:722–730).

Towards the goal of enhancing hepatocyte growth and prolonging liver-specific functions in vitro, hepatic cells have been cultured on various matrices including type I collagen plates and membranes (Michalopoulos and Pitot, 1975, Exp. Cell Res. 94:70–78), homogenized liver biomatrix (Reid et al., 1980, Ann. N.Y. Acad. Sci. 349:70–76), in collagen type IV or laminin-rich gels (Bissell et al., 1987, J. Clin. Invest. 79:801–812), sandwiched between two layers of type I collagen (Dunn et al., 1989, FASEB J. 3:174–177), and on plates coated with fibronectin or the other extracellular matrix proteins (Deschenes et al., 1980, In Vitro 16:722–730). All of these methods have been reported to extend the functional life of hepatocytes in vitro to some extent.

Substantial improvements in this regard were produced by culturing PC with various types of non-parenchymal stromal or littoral hepatic cells or non-hepatic stromal cells. Both human and rat hepatocytes which were co-cultured with liver endothelial cells of the same species maintained specific functions for weeks in culture, although they did not undergo a significant expansion in numbers (Guguen-Guilluozo, et al., 1983, Exp. Cell Res. 143:47–54; Begue et al., 1983, Biochem. Pharmacol. 32:1643–1646). Rat hepatocytes which were co-cultured with human fibroblasts (Kuri-Harcuch and Mendoza-Figueroa, 1989, Differentiation 41:148–157) and endothelial cells (Begue et al., 1983, Biochem. Pharmacol. 32:1643–1646) were reported to sustain cytochrome P-450 activity for more than 10 days. Thus, these mixed hepatocyte co-culture systems may provide microenvironments similar to those in vivo by optimizing cell-cell interactions. In addition, various PC functions may be regulated and/or optimized by other hepatic cells. For example, Kupffer cell secretory products have been reported to modulate PC cytochrome P-450 enzyme activity (Peterson and Renton, 1984, J. Pharmacol. Exp. Ther. 229:299–304). The attachment of PC to fibroblasts is evidently contingent upon the secretion of specialized extracellular matrix substances by Kupffer cells (Michalopoulos et al., 1979, In Vitro 15:769–806). Hepatic endothelial cells also may produce important components of the extracellular matrix (Guguen-Guilluozo, et al., 1983, Exp. Cell Res. 143:47–54), and adipocytes may provide the requisite raw materials for the renewal of cell membranes in metabolically-active hepatocytes.

Although the viability and functional activities of cultured hepatic PC can be prolonged in vitro if. the cells are co-cultured with non-parenchymal liver stromal cells, support cells from other tissues, or their secretory products, PC proliferation is limited or absent in these systems. Mitoses in co-cultures of hepatic cells have been ascribed primarily to non-parenchymal elements (Guguen-Guilluozo, et al., 1983, Exp. Cell Res. 143:47–54). Several reports indicate that non-parenchymal liver cells may express functions similar to hepatocytes (Grisham, 1980, Ann. N.Y. Acad. Sci.

349:128–137) although the nature of these non-PC has not been unequivocally established.

2.2 LIVER TRANSPLANTATION

When bioresorbable polymers were employed as a delivery vehicle for freshly isolated, entrapped hepatocytes into Gunn rats, the normally high circulating levels of bilirubin declined significantly (Asonuma et al., 1992, J. Ped. Res. 27:298–301). Similar effects were achieved in this hyperbilirubinemic animal model using microcarrier-attached hepatocytes (Demetriou et al., 1986, Science 233:1190–1992), liver cells encapsulated within a collagen matrix surrounded by a sodium alginate-poly-L-lysine-sodium alginate membrane (Dixit et al., 1990, Hepatoogy 12:1342–1349) or via direct intrasplenic injection of hepatocytes (Matas et al., 1976, Science 192:892). Other strategies for transplantation include the injection of hepatic cells into previously implanted, vascularized Ivalon sponges (Langer et al., 1993, Science 260:920–926) or polytetrafluoroethylene (PTFE) fibers (Borel-Rinkes et al., 1992, Transplantation 54:210–214). The goal of these techniques is to restore deficient hepatic function resulting from single gene defects and, more broadly, to promote long-term survival from hepatic failure.

Presently, in the United States, donor organs are available for less than one in ten patients that require a transplant (Langer et al., 1993, Science 260:920–926). Paradoxically, the technological gains that have been made in the field of transplantation and the general acceptance of these methods as curative measures have widened the gap between the numbers of organs donated and those who could benefit from a transplant. One potential means to bridge this gap is to expand the amount of tissue that is available through bioengineering. However, a major technical hurdle is that these methods must deliver a sufficient mass of cells to be effective. A conservative estimate is that, in the case of the liver, 10% of the total liver cell number would be required (Asonuma et al., 1992, J. Ped. Res. 27:298–301). Microcarrier and microencapsulation-based methods deliver PC as single cells or in small clusters. The survival lime of these single cells in vivo is limited. In contrast, the entrapped hepatocyte methods concentrate the grafted cells locally and even though immunosuppression is required, close contact between cells is promoted, tissue-like structures develop (Asonuma et al., 1992, J. Ped. Res. 27:298–301; Borel-Rinkes et al., 1992, Transplantation 54:210–214) and the graft will persist for far longer than microencapsulated hepatocytes. These devices have relatively high surface areas and, since they are bioresorbable, they can be grafted into vascular sites such as the omentum or the mesentery (Asonuma et al., 1992, J. Ped. Res. 27:298–301; Uyama et al., 1993, Transplantation 55:932–935; Vacanti et al., 1988, J. Pediatr. Surg. 23:3–9). However, PC survival and growth are difficult to quantify in these constructs and, in the case of the non-biodegradable materials, gradual foreign body compartmentalization by connective tissue elements would be expected. An alterative approach to this problem is using an extracorporeal device containing viable liver cells to overcome the liver function deficit. These have characteristically been hemoperfusion chambers where the blood is separated from the hepatocytes by porous membranes or implantable diffusion chamber-like systems (Langer et al., 1993, Science 260:920–926). Although hepatocytes in these devices are secure from immune challenge, thrombotic problems were associated with the earlier models (Nyberg et al., 1992, Crit. Care Med. 20:1157–1168).

3. SUMMARY OF THE INVENTION

The present invention relates to a three-dimensional cell culture system which can be used to culture a variety of cells and tissues in vitro for prolonged periods of time. In particular, liver PC are inoculated and grown on a pre-established stromal tissue. The stromal tissue comprises stromal cells actively growing on a three-dimensional framework. The stromal tissue provides the support, growth factors, and regulatory factors necessary to sustain long-term active proliferation of liver PC in culture. When grown in this three-dimensional system, the proliferating cells mature and segregate properly to form components of liver tissues analogous to counterparts found in vivo.

The invention is based, in part, on the discovery that growth of stromal cells in three dimensions sustains active proliferation of PC in culture for longer periods of time than conventional monolayer systems. This may be due, in part, to the increased surface area of the three-dimensional support framework which results in a prolonged period of active proliferation of stromal cells. These proliferating stromal cells elaborate proteins, growth factors and regulatory factors necessary to support the long term proliferation of both stromal and PC inoculated onto the stromal tissue. In addition, the three-dimensionality of the framework allows for a spatial distribution which more closely approximates conditions in vivo, thus allowing for the formation of microenvironments conducive to cellular maturation and migration. The growth of cells in the presence of this support may be further enhanced by adding growth or regulatory factors, various ECM and other materials to the support itself or by coating the support with these materials.

The invention is described by way of examples in which adult rat PC are cultured for long-terms in the presence of stromal cells which are grown on a three-dimensional support. Cells derived from the liver PC: stroma co-cultures exhibit a structural and functional heterogeneity as do liver cells in vivo. Proliferation of PC occurs in vitro and appears to be contingent upon the geometry of the culture framework; and, when established on biodegradable framework, these liver PC: stromal cell co-cultures are capable of regenerating a liver-like architecture at ectopic sites and retain their ability to synthesize liver-specific proteins. This. liver cell and tissue culture system may have applications as a substrate for hepatotoxicity testing or in an extracorporeal liver assist device and, when grown on a biogradable polymer framework, to be implanted into subjects with inborn errors of metabolism. Furthermore, genetically engineered liver cells maintain the expression of their exogenous gene long term when grown in the culture system of the present invention.

4. BRIEF DESCRIPTION OF THE DRAWINGS

FIG. 1A. A cytosmear depicting type I (mononuclear) and type II (binuclear) PC stained with Diff-Quik and isolated by "PERCOLL" gradient centrifugation. The smaller stromal elements (arrows) are distinguished from the PC by virtue of their size, nuclear configuration, and nuclear staining density. Original magnification=1,000×.

Figure 1B:
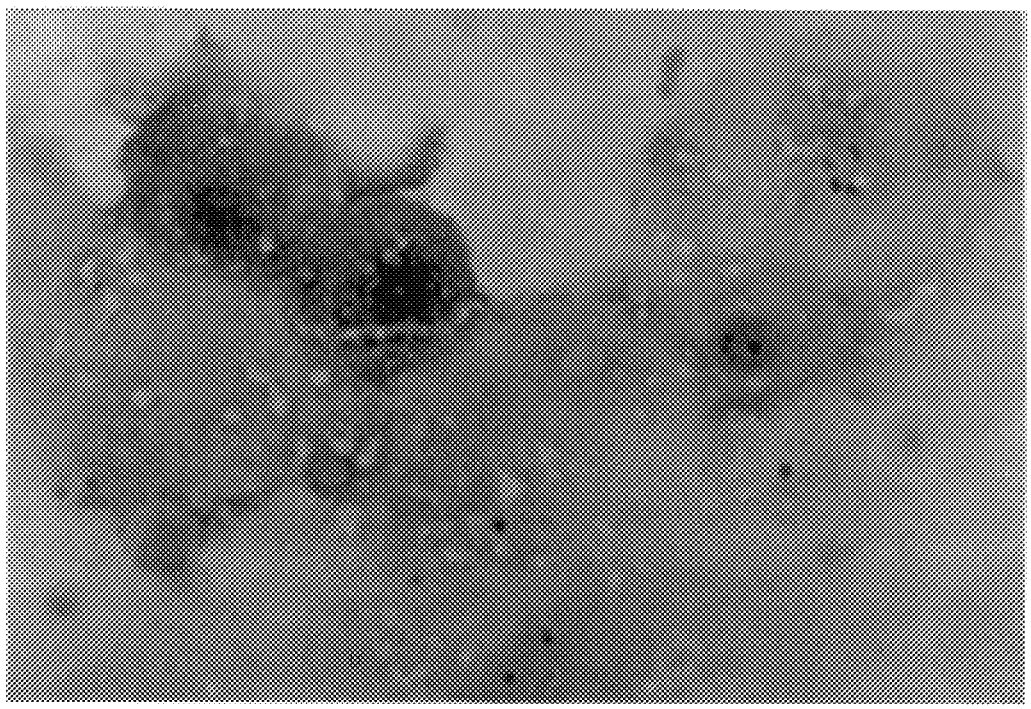

FIG. 1B. Photomicrograph of a cytosmear of cells from the lower band of the discontinuous "PERCOLL" interface (acidophilic cells). This preparation was stained with Diff-Quik for longer periods than was necessary for other hepatocytes in order to visualize their uneven contours, vacuolation, nucleus, and multiple nucleoli. Original magnification=1,000×.

Figure 2A:
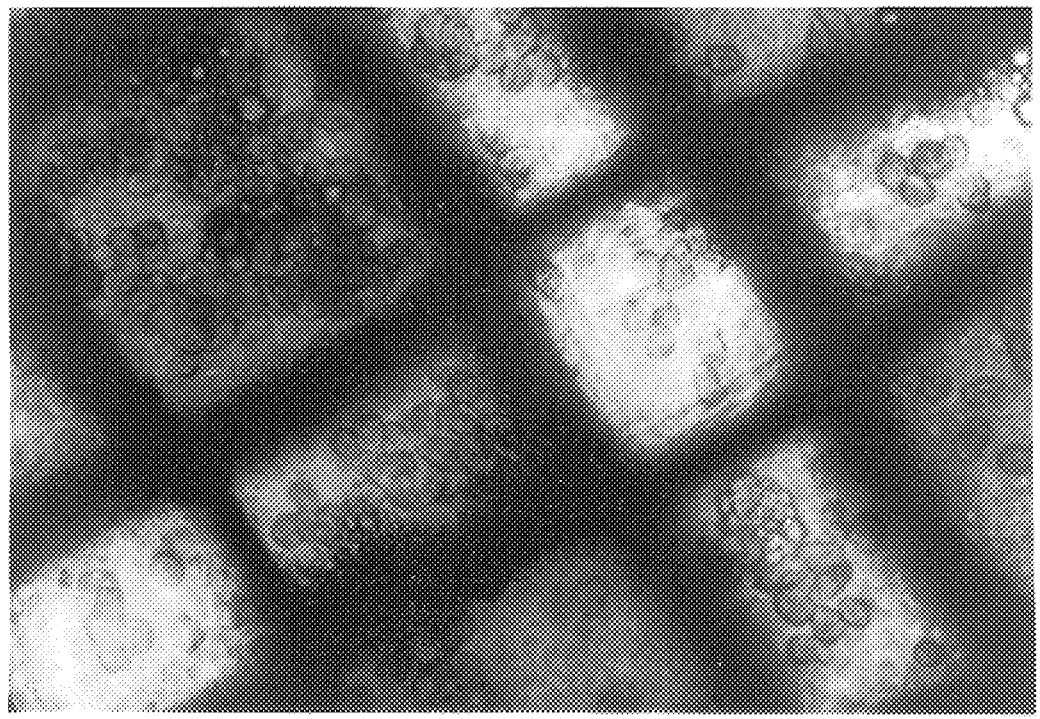

FIG. 2A. Inverted phase photomicrograph of an 8 day old co-culture of various hepatic PC derived from the 70% "PERCOLL" pellet and hepatic stroma on a nylon screen framework. The inoculation with this heterogeneous mixture of cells promotes the growth of morphologically distinct clusters.

Figure 2B:
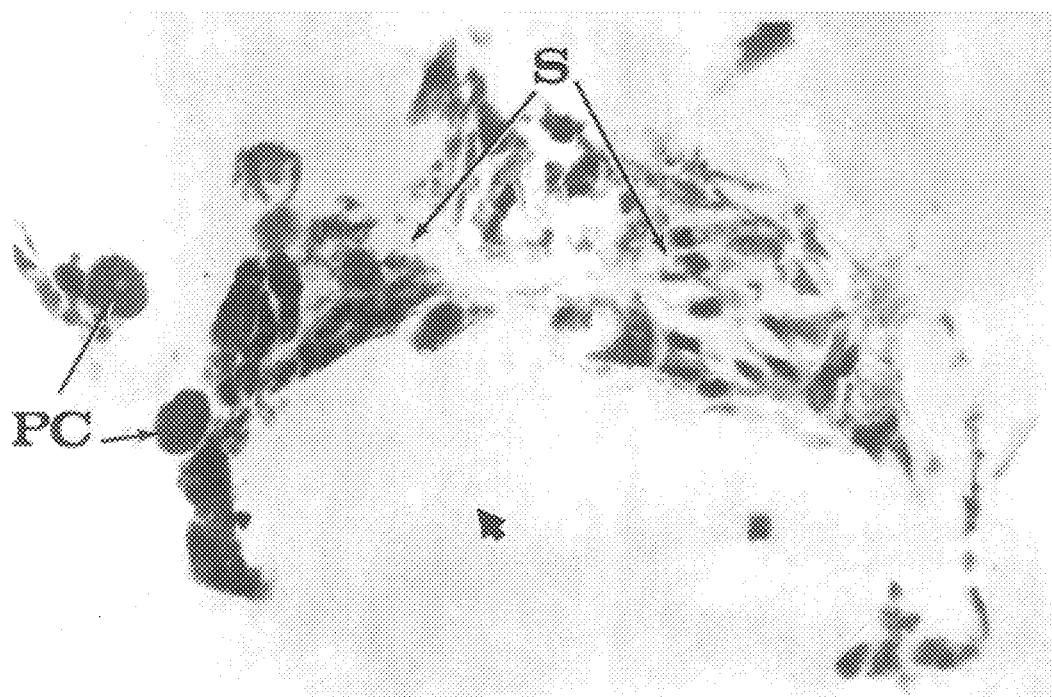

FIG. 2B. Hematoxylin-eosin (H-E) stained section through a liver cell co-culture 24 hr after inoculation of PC. 1,000×. The semicircular space (arrow) denotes the location of the nylon filament. Several round PC are associated with stroma (S).

Figure 2C:
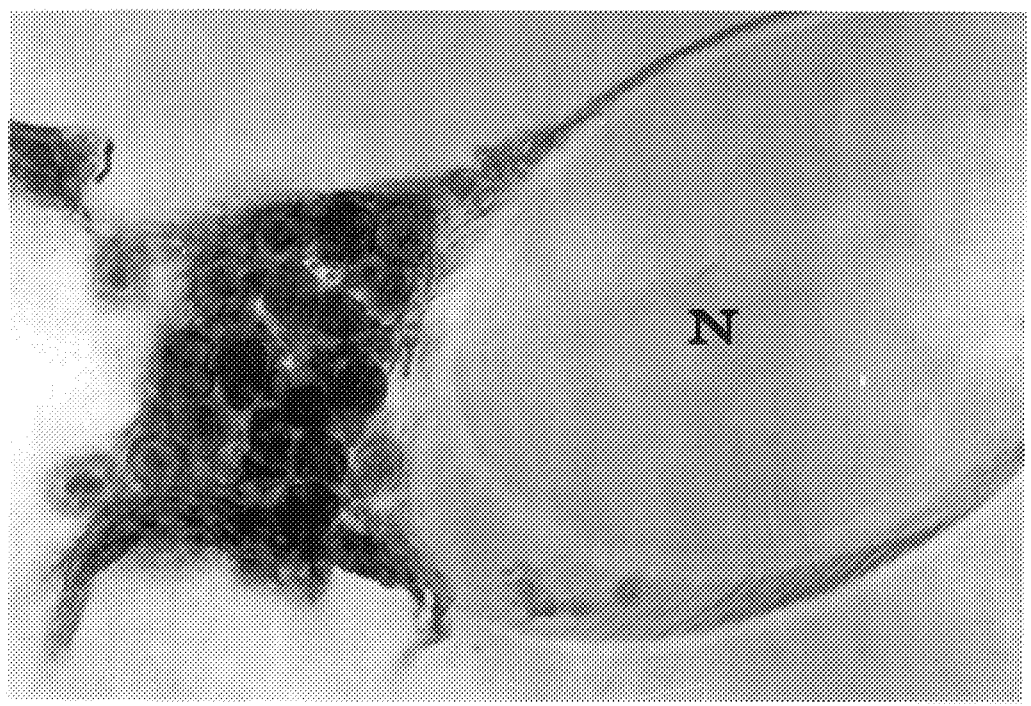

FIG. 2C. H-E stained section through a 52-day old liver cell co-culture. Round PC fill in all of the available space within the template. n=nylon fiber in cross section.

Figure 3A:
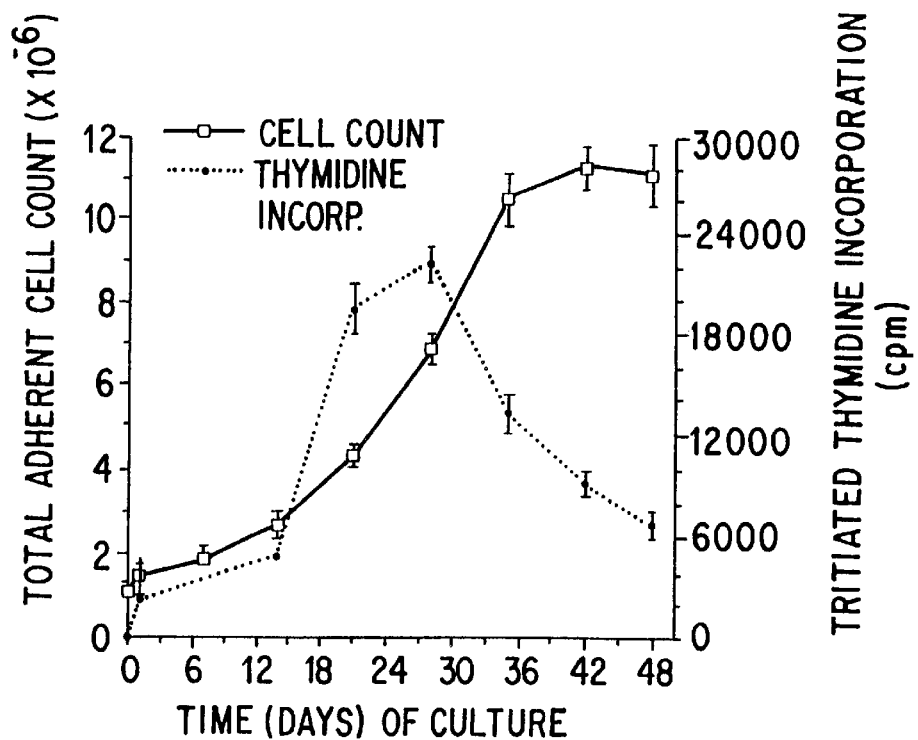

FIG. 3A. The relationship between total adherent cell count and radiothymidine incorporation in liver co-culture. Vertical lines through the means indicate ±1 sem. —□— indicates cell count, and ---●--- indicates thymidine incorporation.

Figure 3B:
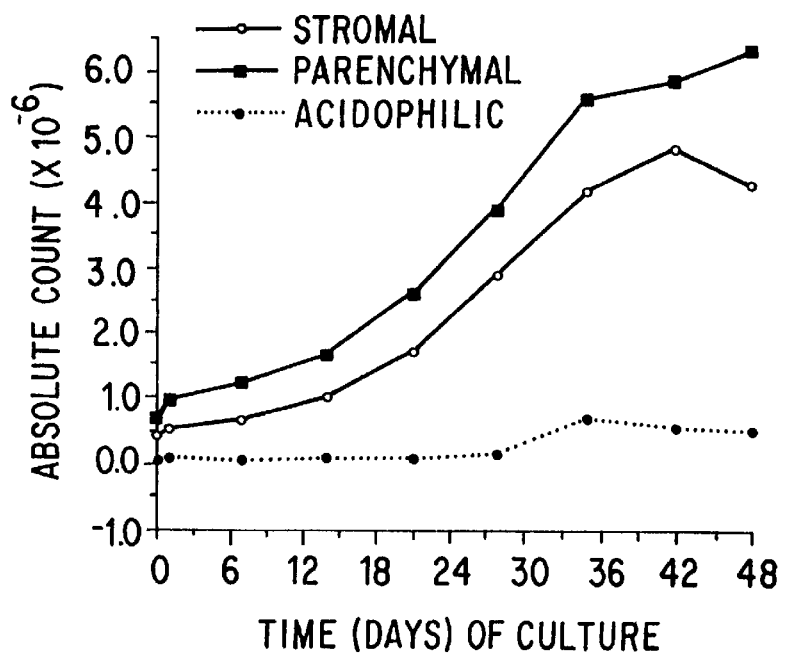

FIG. 3B. Mean differential cell counts in liver co-cultures of various ages. —■— indicates PC, —○— indicates stromal cells, and ---●--- indicates acidophilic cells.

Figure 4A:
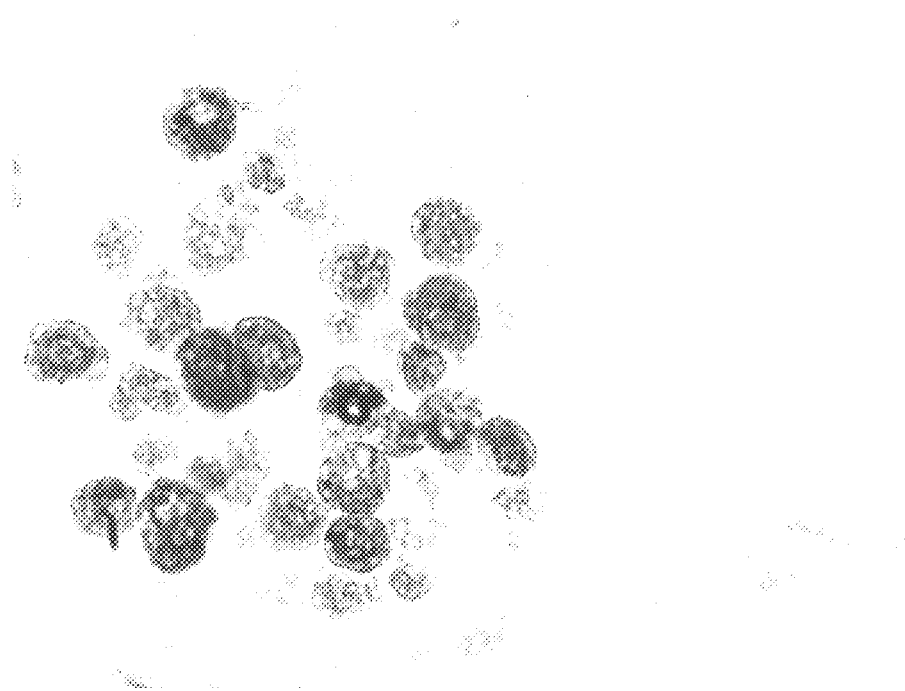

FIG. 4A Section through a 30-day liver co-culture stained with an anti-albumin peroxidase method. There is a range of positivity but albumin expression is highest in the darker cells. The interdigitating stromal cells do not express albumin. n=space occupied by a cross sectioned nylon fiber of the screen.

Figure 4B:
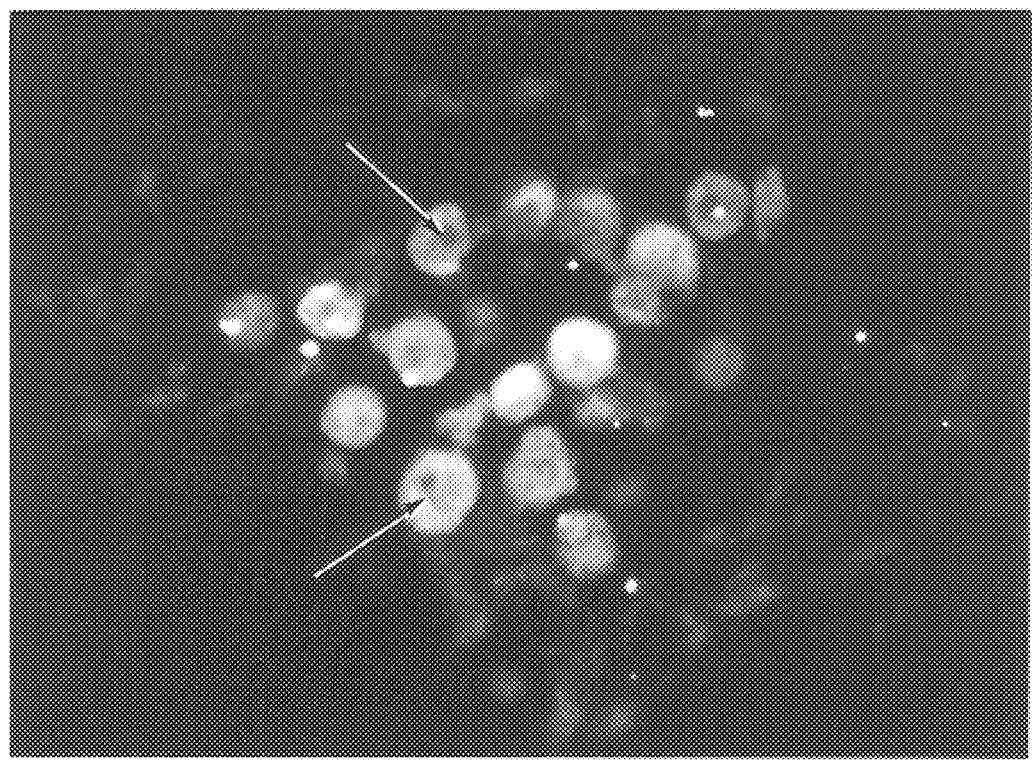

FIG. 4B Section through a 30-day liver co-culture stained with an anti-cytokeratin 19. Immunofluorescence of the large, round cells of the section (arrows). 500×.

Figure 5A:
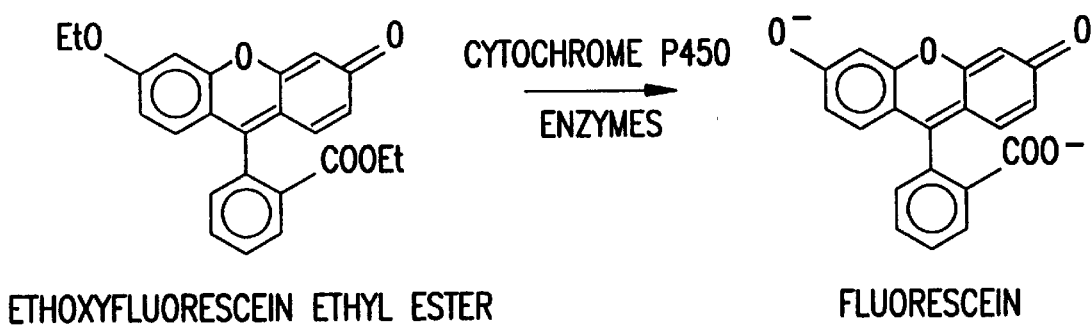

FIG. 5A EFEE is converted by cytochrome P450 enzymes to fluorescein.

Figure 5B:
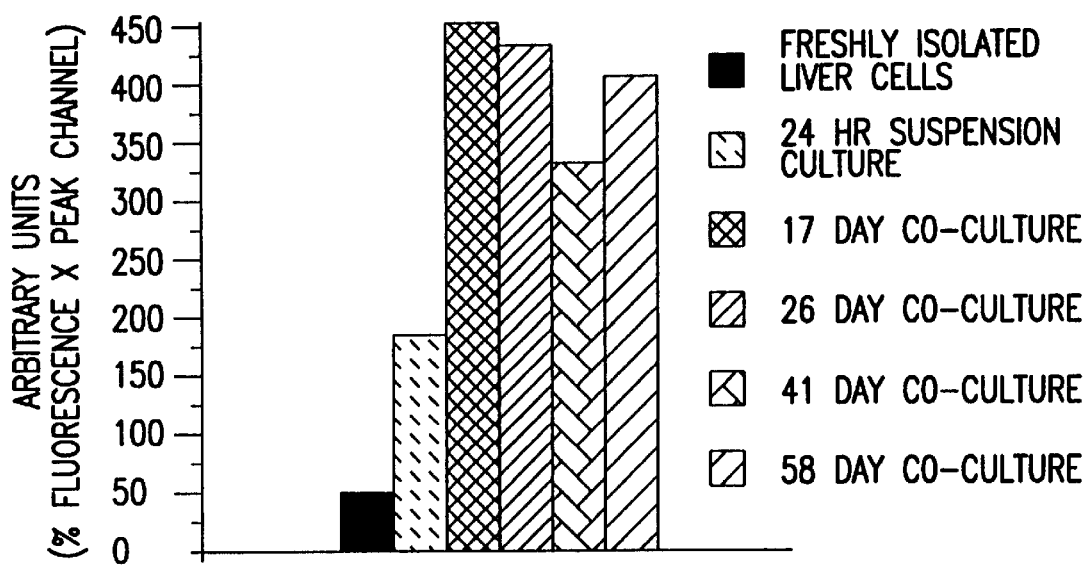

FIG. 5B Cytochrome P450 enzyme activity in hepatic cells 21 hr after the introduction of TCDD. The EFEE to fluorescein conversion reaction is quantified as the product of the percentage of positively fluorescent cells and the peak fluorescence channel number. The number of events measured for each sample is 10,000–20,000.

Figure 6:
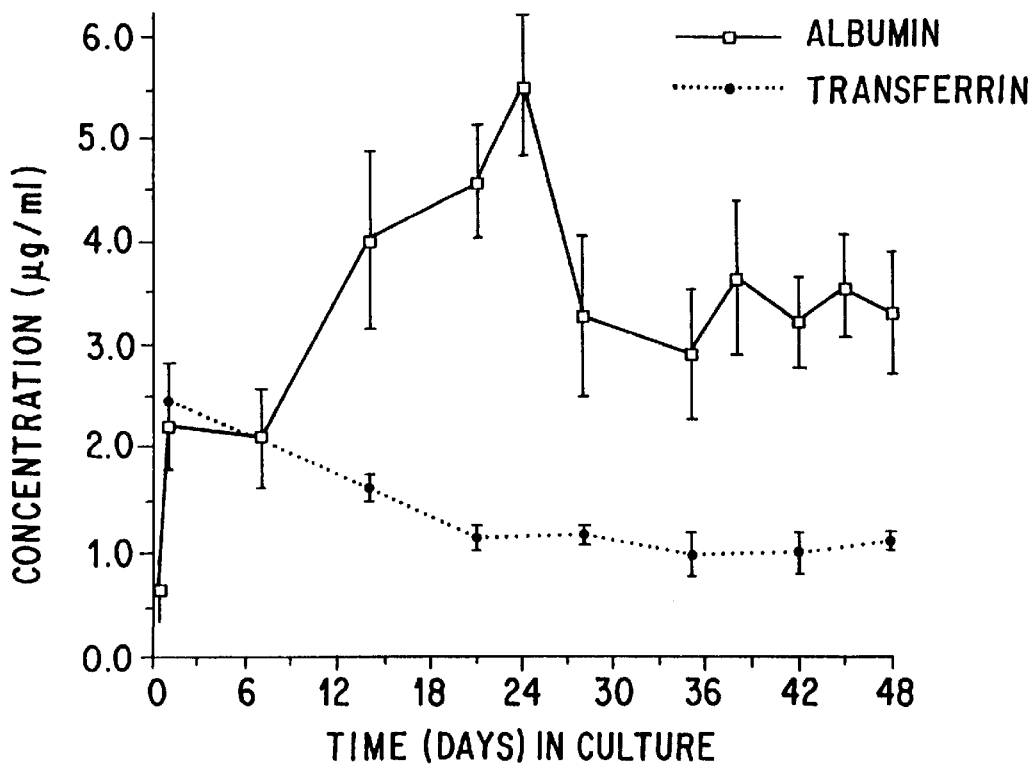

FIG. 6 Mean quantities of albumin and transferrin present in the medium at various intervals of culture. Vertical lines through the means=±1 sem. —□— indicates albumin and ---●--- incidates transferrin.

Figure 7:
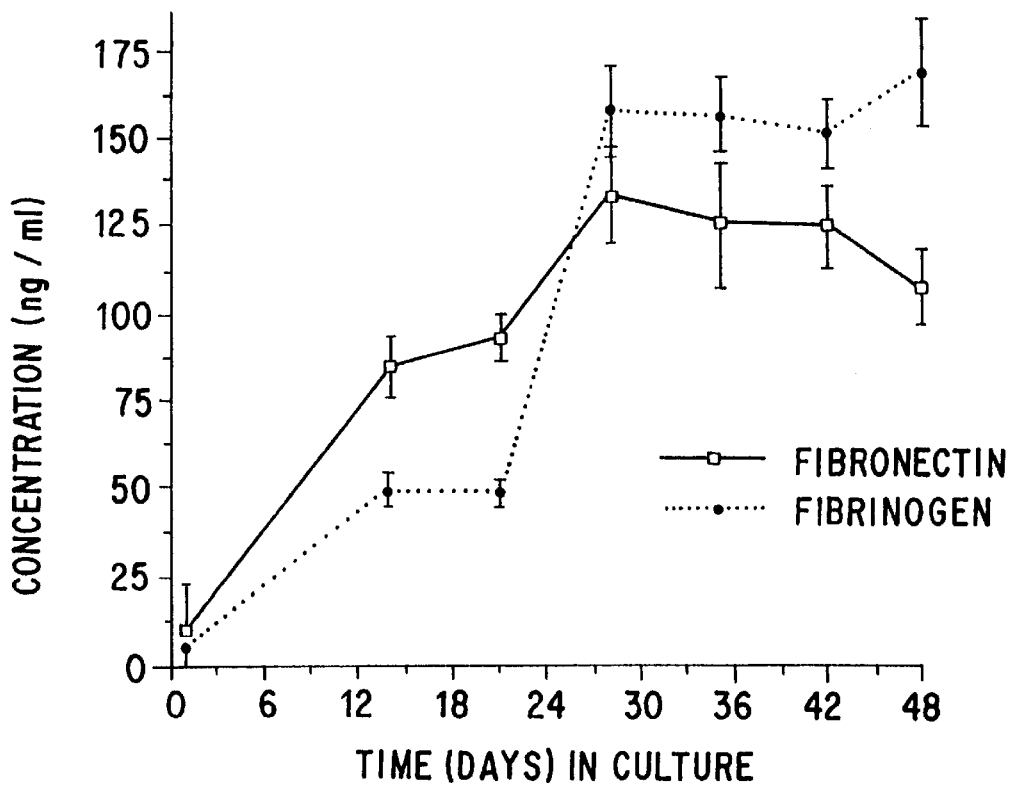

FIG. 7 Mean quantities of fibrinogen and fibronectin present in the medium at various intervals of culture. Vertical lines through the means=±1 sem. —□— indicates fibronectin, and ---●--- indicates fibrionogen.

Figure 8A:
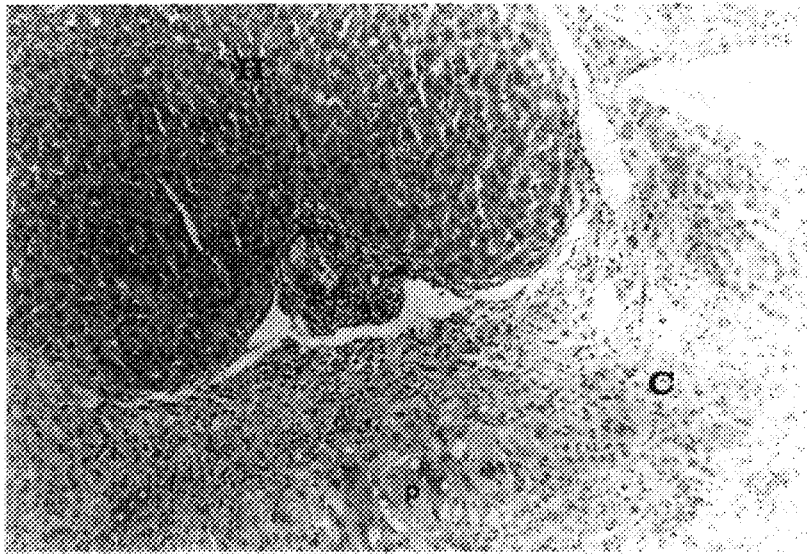

FIG. 8A Photomicrographs of co-cultures of liver PC and stromal cells on PGA felt 30 days after grafting into Long-Evans rats. H and E staining. Low power view of a subcutaneous graft showing a focus of hepatic tissue (H) contiguous to connective tissue (C) in the process of reorganization. A tract of residual, partially hydrolyzed PGA polymers (p) is present. Arrows identify putative biliary structures associated with the regenerating hepatic tissue. 100×.

Figure 8B:
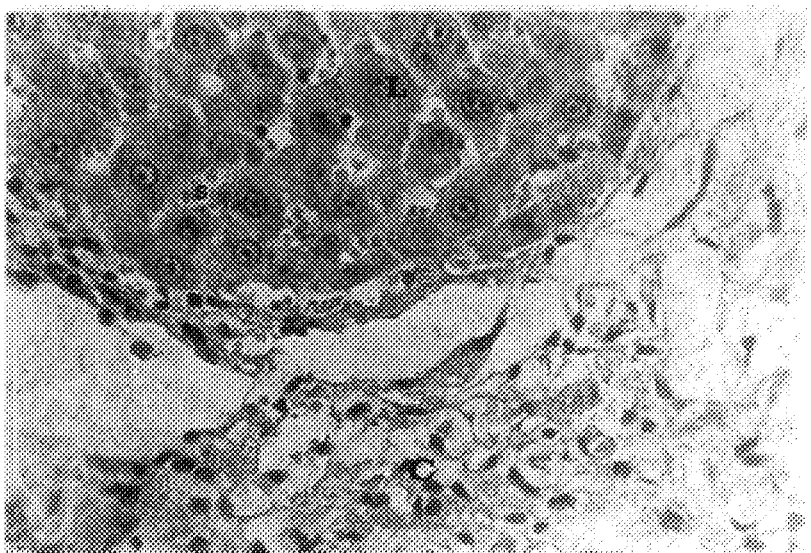

FIG. 8B. Photomicrographs of co-cultures of liver PC and stromal cells on PGA felt 30 days after grafting. The interface between grafted liver co-cultures (L) and connective tissue (C) elements of the omentum. Sinusoids (s) are evident.

Figure 8C:
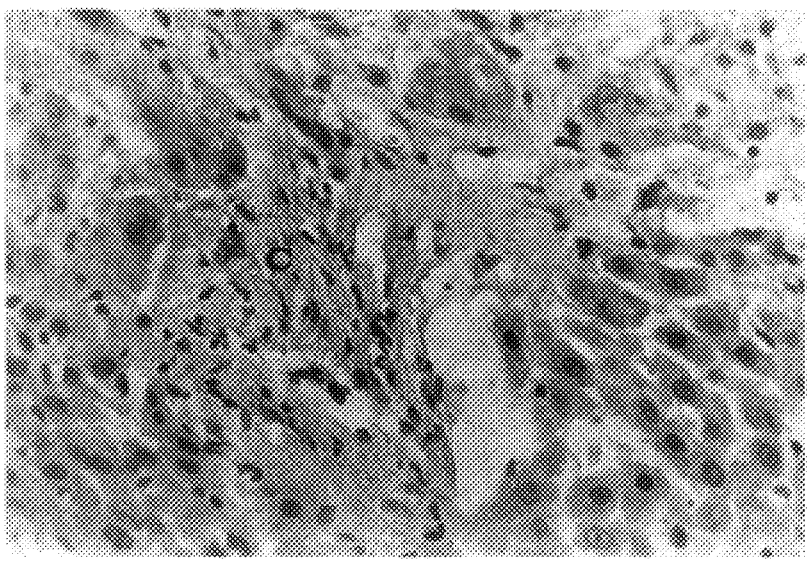

FIG. 8C Photomicrographs of co-cultures of liver PC and stromal cells on PGA felt 30 days after grafting. Graft site in the mesentery showing PC with sinusoids (lower right), connective tissue in the process of repair (C), and PC interspersed between connective tissue elements in the absence of developing sinusoidal structures (top left). 500×.

5. DETAILED DESCRIPTION OF THE INVENTION

The present invention involves a three-dimensional framework and its use as the support for a three-dimensional, multi-layer cell culture system. In previously known tissue culture systems, the cells were grown in a monolayer. Cells cultured on a three-dimensional stromal framework, in accordance with the present invention, grow in multiple layers, forming a tissue. This stromal tissue approaches physiologic conditions found in vivo to a greater degree than previously described monolayer tissue culture systems. The three-dimensional cell culture system is applicable to the proliferation of liver cells and formation of liver tissues.

The culture system has a variety of applications. For liver tissues, the three-dimensional culture itself may be transplanted or implanted into a living organism. The three-dimensional cultures may also be used in vitro for cytotoxicity testing and screening compounds. In yet another application, the three-dimensional culture system may be used as a "bioreactor" to produce cellular products in large quantities, including products of exogenous genes transferred into the cultured cells.

In accordance with the invention, liver PC are inoculated and cultured on a pre-established three-dimensional stromal tissue. The stromal tissue comprises stromal cells grown on a three-dimensional matrix or framework. The stromal cells comprise fibroblasts with or without additional cells and/or elements described more fully herein. The fibroblasts and other cells and/or elements that comprise the stroma may be fetal or adult in origin, and may be derived from convenient sources such as skin, liver, pancreas, etc. Such tissues and/or organs can be obtained by appropriate biopsy or upon autopsy. In fact, cadaver organs may be used to provide a generous supply of stromal cells and elements.

Neonatal fibroblasts may support the growth of many different cells and tissues in the three-dimensional culture system, and, therefore, can be inoculated onto the matrix to form a "generic" stromal tissue for culturing any of a variety of cells and tissues, including liver PC. However, in certain instances, it may be preferable to use a "specific" rather than "generic" stromal tissue, in which case stromal cells and elements can be obtained from a liver tissue. For example, where the three-dimensional culture is to be used for purposes of transplantation or implantation in vivo, it may be preferable to obtain the stromal cells and elements from the individual who is to receive the transplant or implant. This approach might be especially advantageous where immunological rejection of the transplant and/or graft versus host disease is likely. Moreover, fibroblasts and other stromal cells and/or elements may be derived from the same type of tissue to be cultured in the three-dimensional system. This might be advantageous when culturing liver tissues in which specialized stromal cells may play particular structural/functional roles; e.g., Kupffer cells of liver.

Once inoculated onto the three-dimensional framework, the stromal cells will proliferate on the framework and support the growth of liver PC inoculated into the three-dimensional culture system of the invention. In fact, when inoculated with the liver PC, the three-dimensional stromal tissue will sustain active proliferation of the culture for long periods of time. Growth and regulatory factors may be added to the culture, but are not necessary since they are elaborated by the stromal tissue.

Because, according to the invention, it is important to recreate, in culture, the cellular microenvironment found in vivo for a particular tissue, the extent to which the stromal cells are grown prior to inoculation of PC may vary depending on the type of tissue to be grown in three-dimensional tissue culture. Importantly, because openings in the mesh permit the exit of stromal cells in culture, confluent stromal cultures do not exhibit contact inhibition, and the stromal cells continue to grow, divide, and remain functionally active.

The invention is based, in part, upon the discovery that growth of the stromal cells in three dimensions will sustain active proliferation of both the stromal and tissue-specific cells in culture for much longer time periods than will monolayer systems. Moreover, the three-dimensional system supports the maturation, differentiation, and segregation of liver cells in culture in vitro to form components of adult liver tissues analogous to counterparts found in vivo.

Although the Applicants are under no duty or obligation to explain the mechanism by which the invention works, a number of factors inherent in the three-dimensional culture system may contribute to its success:

(a) The three-dimensional framework provides a greater surface area for protein deposition, and consequently, for the adherence of stromal cells.

(b) Because of the three-dimensionality of the framework, stromal cells continue to actively grow, in contrast to cells in monolayer cultures, which grow to confluence, exhibit contact inhibition, and cease to grow and divide. The elaboration of growth and regulatory factors by replicating stromal cells may be partially responsible for stimulating proliferation and regulating differentiation of cells in culture.

(c) The three-dimensional framework allows for a spatial distribution of cellular elements which is more analogous to that found in the counterpart tissue in vivo.

(d) The increase in potential volume for cell growth in the three-dimensional system may allow the establishment of localized microenvironments conducive to cellular maturation.

(e) The three-dimensional framework maximizes cell-cell interactions by allowing greater potential for movement of migratory cells, and for the establishment of communications between PC and the various types of stromal cells such as macrophages, in the adherent layer.

(f) It has been recognized that maintenance of a differentiated cellular phenotype requires not only growth/differentiation factors but also the appropriate cellular interactions. The present invention effectively recreates the tissue microenvironment.

The three-dimensional stromal support, the culture system itself, and its maintenance, as well as various uses of the three-dimensional cultures are described in greater detail in the subsections below.

5.1. ESTABLISHMENT OF THREE-DIMENSIONAL STROMAL MATRIX

The three-dimensional support framework may be of any material and/or shape that: (a) allows cells to attach to it (or can be modified to allow cells to attach to it); and (b) allows cells to grow in more than one layer. A number of different materials may be used to form the framework, including but not limited to: nylon (polyamides), dacron (polyesters), polystyrene, polypropylene, polyacrylates, polyvinyl compounds (e.g., polyvinylchloride), polycarbonate (PVC), polytetrafluorethylene (PTFE; teflon), thermanox (TPX), nitrocellulose, cotton, polyglycolic acid (PGA), cat gut sutures, cellulose, gelatin, dextran, etc. Any of these materials may be woven into a mesh, for example, to form the three-dimensional framework. Certain materials, such as nylon, polystyrene, etc., are poor substrates for cellular attachment. When these materials are used as the three-dimensional support framework, it is advisable to pre-treat the matrix prior to inoculation of stromal cells in order to enhance the attachment of stromal cells to the framework. For example, prior to inoculation with stromal cells, nylon screens could be treated with 0.1M acetic acid, and incubated in polylysine, FBS, and/or collagen to coat the nylon. Polystyrene could be similarly treated using sulfuric acid.

Where the three-dimensional culture is itself to be implanted in vivo, it may be preferable to use biodegradable materials such as PGA, catgut suture material, collagen, polylactic acid, or hyaluronic acid. For example, these materials may be woven into a three-dimensional framework such as a collagen sponge. Where the cultures are to be maintained for long periods of time or crypreserved, non-degradable materials such as nylon, dacron, polystyrene, polyacrylates, polyvinyls, teflons, cotton, etc. may be preferred. A convenient nylon mesh which could be used in accordance with the invention is Nitex, a nylon filtration mesh having an average pore size of 140 $\mu$m and an average nylon fiber diameter of 90 $\mu$m (#3-210/36, Tetko, Inc., N.Y.).

Stromal cells comprising fibroblasts, with or without other cells and elements described below, are inoculated onto the framework. These stromal cells may be derived from organs, such as skin, liver, pancreas, etc. which can be obtained by biopsy (where appropriate) or upon autopsy. In fact fibroblasts can be obtained in quantity rather conveniently from any appropriate cadaver organ. As previously explained, fetal fibroblasts can be used to form a "generic" three-dimensional stromal tissue that will support the growth of a variety of different cells and/or tissues. However, a "specific" stromal tissue may be prepared by inoculating the three-dimensional framework with stromal cells derived from the liver and/or from a particular individual who is later to receive the cells and/or tissues grown in culture in accordance with the three-dimensional system of the invention. Liver stromal cells include but are not limited to Kupffer cells, endothelial cells, fat storing cells and fibroblasts.

Stromal cells may be readily isolated by disaggregating an appropriate organ or tissue. This may be readily accomplished using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase, dispase etc. Mechanical disruption can also be accomplished by a number of methods including, but not limited to the use of grinders, blenders, sieves, homogenizers, pressure cells, or insonators to name but a few. For a review of tissue disaggregation techniques, see Freshney, Culture of Animal Cells. A Manual of Basic Technique, 2d Ed., A. R. Liss, Inc., New York, 1987, Ch. 9, pp. 107–126.

Once the tissue has been reduced to a suspension of individual cells, the suspension can be fractionated into subpopulations from which the fibroblasts and/or other stromal cells and/or elements can be obtained. This also may be accomplished using standard techniques for cell separation including but not limited to cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, countercurrent distribution, electrophoresis and fluorescence-activated cell sorting. For a review of clonal selection and cell separation techniques, see Freshney, Culture of Animal Cells. A Manual of Basic Techniques, 2d Ed., A. R. Liss, Inc., New York, 1987, Ch. 11 and 12, pp. 137–168.

The isolation of stromal cells may, for example, be carried out as follows: fresh tissue samples are thoroughly washed and minced in Hanks balanced salt solution (HBSS) in order to remove serum. The minced tissue is incubated from 1–12 hours in a freshly prepared solution of a dissociating enzyme such as trypsin. After such incubation, the dissociated cells are suspended, pelleted by centrifugation and plated onto culture dishes. All stromal cells will attach before other cells, therefore, appropriate stromal cells can be selectively isolated and grown. The isolated stromal cells can then be grown to confluency, lifted from the confluent culture and inoculated onto the three-dimensional framework (see, Naughton et al., 1987, J. Med. 18(3&4):219–250). Inoculation of the three-dimensional framework with a high concentration of stromal cells, e.g., approximately $10^6$ to $5 \times 10^7$ cells/ml, will result in the establishment of the three-dimensional stromal tissue in shorter periods of time.

In addition to fibroblasts, other cells may be added to form the three-dimensional stromal tissue required to support long-term growth in culture. For example, other cells found in loose connective tissue may be inoculated onto the three-dimensional framework along with fibroblasts. Such cells include but are not limited to endothelial cells, pericytes, macrophages, monocytes, adipocytes, etc. These stromal cells may readily be derived from appropriate organs such as skin, liver, etc., using methods known in the art such as those discussed above. In a specific embodiment of the invention, liver stromal cells which include Kupffer cells, endothelial cells, adipocytes and fibroblasts are inoculated onto the framework collectively.

Again, where the cultured cells are to be used for transplantation or implantation in vivo it is preferable to obtain the stromal cells from the patient's own tissues. The growth of cells in the presence of the three-dimensional stromal support framework may be further enhanced by adding to the framework, or coating it with proteins (e.g., collagens, elastin fibers, reticular fibers) glycoproteins, glycosaminoglycans (e.g., heparan sulfate, chondroitin-4-sulfate, chondroitin-6-sulfate, dermatan sulfate, keratan sulfate, etc.), a cellular matrix, and/or other materials.

After inoculation of the stromal cells, the three-dimensional framework should be incubated in an appropriate nutrient medium. Many commercially available media such as RPMI 1640, Fisher's, Iscove's, Mccoy's, and the like may be suitable for use. It is important that the three-dimensional stromal tissue be suspended in the medium during the incubation period in order to maximize proliferative activity. In addition, the culture should be "fed" periodically to remove the spent media, depopulate released cells, and add fresh media.

During the incubation period, the stromal cells will grow linearly along and envelop the filaments of the three-dimensional framework before beginning to grow into the openings of the framework. It is important to grow the cells to an appropriate degree which reflects the proportion of stromal cells present in the in vivo tissue prior to inoculation of the stromal tissue with the PC.

The openings of the framework should be of an appropriate size to allow the stromal cells to stretch across the openings. Maintaining actively growing stromal cells which stretch across the framework enhances the production of growth factors which are elaborated by the stromal cells, and hence will support long term cultures. For example, if the openings are too small, the stromal cells may rapidly achieve confluence but be unable to easily exit from the mesh; trapped cells may exhibit contact inhibition and cease production of the appropriate factors necessary to support proliferation and maintain long term cultures. If the openings are too large, the stromal cells may be unable to stretch across the opening; this will also decrease stromal cell production of the appropriate factors necessary to support proliferation and maintain long term cultures. When using a mesh type of framework, as exemplified herein, it has been found that openings ranging from about 140 $\mu$m to about 220 $\mu$m will work satisfactorily. However, depending upon the three-dimensional structure and intricacy of the framework, other sizes may work equally well. In fact, any shape or structure that allows the stromal cells to stretch and continue to replicate and grow for lengthy time periods will work in accordance with the invention.

Different proportions of the various types of collagen deposited on the matrix can affect the growth of the later inoculated PC. The proportions of ECM proteins deposited can be manipulated or enhanced by selecting fibroblasts which elaborate the appropriate collagen type. This can be accomplished using monoclonal antibodies of an appropriate isotype or subclass that is capable of activating complement, and which define particular collagen types. These antibodies and complement can be used to negatively select the fibroblasts which express the desired collagen type. Alternatively, the stroma used to inoculate the framework can be a mixture of cells which synthesize the appropriate collagen types desired. The distribution and origins of the five types of collagen is shown in Table I.

TABLE I

DISTRIBUTIONS AND ORIGINS OF THE FIVE TYPES OF COLLAGEN

| Collagen Type | Principal Tissue Distribution | Cells of Origin |
| --- | --- | --- |
| I | Loose and dense ordinary connective tissue; collagen fibers | Fibroblasts and reticular cells; smooth muscle cells |
|  | Fibrocartilage | cells |
|  | Bone | Osteoblast |
|  | Dentin | Odontoblasts |
| II | Hyaline and elastic cartilage | Chondrocytes |
|  | Vitreous body of eye | Retinal cells |
| III | Loose connective tissue; reticular fibers | Fibroblasts and reticular cells |
|  | Papillary layer of dermis | Smooth muscle cells; endo- |
|  | Blood vessels | thelial cells |
| IV | Basement membranes | Epithelial and endothelial cells |
|  | Lens capsule of eye | Lens fibers |
| V | Fetal membranes; placenta | Fibroblasts |
|  | Basement membranes |  |
|  | Bone |  |
|  | Smooth muscle | Smooth muscle cells |

Thus, since the three-dimensional culture system described herein is suitable for the growth of diverse cell types and tissues, and depending upon the tissue to be cultured and the collagen types desired, the appropriate stromal cell(s) may be selected to inoculate the three-dimensional framework. However, for the practice of the present invention, stromal cells isolated from the liver are preferred for use to support the growth of liver PC.

During incubation of the three-dimensional stromal support, proliferating cells may be released from the framework. These released cells may stick to the walls of the culture vessel where they may continue to proliferate and form a confluent monolayer. This should be prevented or minimized, for example, by removal of the released cells during feeding, or by transferring, the three-dimensional stromal tissue to a new culture vessel. The presence of a confluent monolayer in the vessel may "shut down" the growth of cells in the three-dimensional culture. Removal of the confluent monolayer or transfer of the stromal tissue to fresh media in a new vessel will restore proliferative activity of the three-dimensional culture system. Such removal or transfers should be done in any culture vessel which has a stromal monolayer exceeding 25% confluency. Alternatively, the culture system could be agitated to prevent the released cells from sticking, or instead of periodically feeding the cultures, the culture system could be set up so that fresh media continuously flows through the system. The flow rate could be adjusted to both maximize proliferation within the three-dimensional culture, and to wash out and remove cells released from the matrix, so that they will not stick to the walls of the vessel and grow to confluence. In any case, the released stromal cells can be collected and crypreserved for future use.

5.2. THREE-DIMENSIONAL LIVER TISSUE CULTURE SYSTEM

Hepatocytes may be isolated by conventional methods (Berry and Friend, 1969, J. Cell Biol. 43:506– 520) which can be adapted for human liver biopsy or autopsy material. Briefly, a cannula is introduced into the portal vein or a portal branch and the liver is perfused with calcium-free or magnesium-free buffer until the tissue appears pale. The organ is then perfused with a proteolytic enzyme such as a collagenase solution at an adequate flow rate. This should digest the connective tissue framework. The liver is then washed in buffer and the cells are dispersed. The cell suspension may be filtered through a 70 $\mu$m nylon mesh to remove debris. Hepatocytes may be selected from the cell suspension by two or three differential centrifugations.

For perfusion of individual lobes of excised human liver, HEPES buffer may be used. Perfusion of collagenase in HEPES buffer may be accomplished at the rate of about 30 ml/minute. A single cell suspension is obtained by further incubation with collagenase for 15–20 minutes at 37° C. (Guguen-Guillouzo and Guillouzo, eds, 1986, "Isolated and Culture Hepatocytes" Paris, INSERM, and London, John Libbey Eurotext, pp.1–12; 1982, Cell Biol. Int. Rep. 6:625–628).

The isolated hepatocytes may then be used to inoculate the three dimensional stromal tissue. Hepatic PC function in vitro can be maintained over longer time periods if they are cultured with various ECM substances or co-cultured with other cell types, although cellular proliferation is low or absent in these systems after the first several days of culture (Michalopoulos et al., 1975, Exp. Cell Res. 94:70–78; Dunn et al., 1989, FASEB J. 3:174–177; Reid et al., 1980, Ann. N.Y. Acad. Sci. 349:70–76; Bissell, et al., 1987, J. Clin. Invest. 79:801–812; Deschenes et al., 1980, In Vitro 16:722–730; Guguen-Guilluozo et al., 1983, Exp. Cell Res. 143:47–54; Begue et al., 1983, Biochem. Pharmacol. 32:1643–1646; Kuri-Harcuch et al, 1989, Differentiation 41:148–157).

Furthermore, liver cultures are often difficult to evaluate. Several reasons for this include: mitoses in co-cultures of hepatic cells have been ascribed to non-parenchymal elements (Guguen-Guilluozo et al., 1983, Exp. Cell Res. 143:47–54), non-parenchymal liver cells have been reported to express functions similar to hepatocytes such as albumin synthesis (Hayner et al. 1988., Cancer Res. 48:368–378), and hepatocyte phenotypes appear to change under some culture conditions even though PC and hepatic stroma remain morphologically distinct (Grisham, 1980, Ann. N.Y. Acad. Sci. 349:128–137).

Three dimensional frameworks such as the nylon screens not only provide an increased surface area for cell growth but apparently allow hepatic PC and stromal cells to form a microenvironment conducive to expression of liver-specific metabolic activity as well as PC proliferation. PC that are inoculated onto a three-dimensional framework containing the various types of liver stromal cells synthesize albumin, fibrinogen, transferrin and other proteins, and display TCDD-inducible cP450 activity for 2 months in culture. Growth of PC is evident in association with these stroma and proceeds until all available space for expansion within the framework is exhausted. Albumin secretion by PC increases by >700% over 'time zero' levels by 24 days of co-culture (0.66±0.32 vs. 5.5±0.70 $\mu$g/ml; P≦0.01) and although the levels drop thereafter, they remain ~400% greater than input levels at 48 days of co-culture (0.66±0.32 vs. 3.28±0.59 $\mu$g/ml; P≦0.025). This result compares favorably to the monolayer-based co-culture system of Guguen-Guilluozo et al who reported peak albumin levels at ~+300% of input cells after 10 days of co-culture but observed a steady decline thereafter until 42 days when the levels of this protein were essentially equal to the quantities secreted by input cells (Guguen-Guilluozo et al., 1983, Exp. Cell Res. 143:47–54). In the three-dimensional nylon screen co-cultures, albumin synthesis, and possibly the production of other proteins, are related to proliferative activity and/or the cell density of the framework. As the nylon screens become filled with PC, $^3$H-thymidine incorporation and cell division drop dramatically; albumin and fibronectin synthesis also decrease as the cultures reach their maximum capacity of total cells. This decline of albumin synthesis is the result of decreased metabolic activities of these cells, and it is not a loss of liver specific function. The three-dimensional culture system of the present invention maximizes cell-cell contact which enhances hepatocyte protein synthesis in vitro.

Although PC proliferation is difficult to quantify in co-cultures because of the presence of other cell types, PC growth is evident in histological sections through the three-dimensional cultures. PC are the largest cells of the co-culture and unlike stroma, which are irregularly-shaped and branched cells, are round. These large, round cells stain positively for the liver PC-associated proteins albumin, fibrinogen, transferrin, and cytokeratin 19. This finding is confirmed by differential counts of cells derived from the co-cultures in which PC are distinguished from non-PC by virtue of their size, nuclear: cytoplasmic volume, nuclear characteristics, and lack of ability to phagocytose colloidal carbon and react with antibodies directed against endothelial cell epitopes. These findings, coupled with radiothymidine incorporation studies, indicate that PC proliferation occurs over a ≧4 week period in the present three dimensional model. Such a phenomenon has not been demonstrated in any other liver culture systems for longer than 1 week. A limiting aspect of this cell expansion appears to be space. PC grow only in association with stroma and their rates of growth decline as the framework become filled with cells.

Although it appears that most PC have the capacity to synthesize albumin in vivo, the quantity and rate of expression of this protein varies with location within the acinus (Bernuau et al., 1981, Biol. Cell 40:17–22; Guillouzo et al., 1982, Biol. Cell 43:163–171). In contrast to normal conditions where only 15–20% of the total liver PC strongly express albumin (Schreiber et al., 1970, J. Cell Biol. 47:285–290; Araki et al., 1992, Acta Anat. 143:169–177), virtually all PC express this protein following hepatotoxic injury (Araki et al., 1992, Acta Anat. 143:169–177) or in response to perturbations in plasma proteins associated with nephrotic syndrome (Maurice et al., 1979, Lab. Invest. 40:39–45). It is possible that initially, most PC inoculated onto the nylon screen/stromal tissue synthesize albumin and that this model, in some respects, resembles regenerating or injured liver. As PC fill the framework, their proliferation rate slows, and albumin as well as fibronectin synthesis decline in the majority of the cells, presumably because of ECM or other microenvironmental factors. In this respect, ECM substances influence cell division and gene expression in hepatic cells (Michalopoulos et al., 1979, In Vitro 15:796–805; Bernuau et al., 1981, Biol. Cell 40:17–22) and albumin synthesis in cultured hepatocytes can be induced by certain ECM proteins (Michalopoulos et al., 1979, In Vitro 15:796–805; Tonomura et al., 1987, J. Cell Physiol. 130:221–227).

Likewise, PC functional heterogeneity has been described by a number of investigators and purportedly is influenced by several factors including: blood gas and nutrient gradients across the acinus (Matsumara et al., 1983, Amer. J. Physiol. 244:G656–659), microenvironmental differences (Martinez-Hernandez et al., 1993, In: Extracellular Matrix:Chemistry, Biology, Pathology, Zern and Reid, Eds. Marcel-Dekker, NY), and maturational gradients of PC from the portal region (immature) to the terminal hepatic vein (mature) (Arber et al., 1988, Liver 8:80–87). The cultures of the present invention display a number of liver-specific functions for up to 7 weeks in culture, including TCDD-inducible cP450 enzyme activity. Although the three populations of hepatic cells that are resolved by flow cytometry all exhibit some ability to convert EFEE to fluorescein, the highest activity is observed in the PC populations.

The characteristics of cell growth on three-dimensional frameworks are intrinsically different from that on flat-bottomed plastic flasks. For example, the cell matrix deposition is enhanced, but proliferation rate is lower when stromal cells are cultured on nylon screens as compared to plastic flasks. This three-dimensional framework may also enhance the opportunity for normal cell-cell interactions and orientation, thereby permitting the various subpopulations of cells to act deterministically to form a tissue-like construct. In this regard, the presence of inhibitors in serum has been hypothesized as a potential reason why PC fail to proliferate in culture (Barnes and Sato, 1980, Cell 22:649–655) and serum factors have been reported to contribute to the appearance of the large, bizarre, and putatively de-differentiated masses of PC in monolayer cultures (Grisham, 1980, Ann. N.Y. Acad. Sci. 349:128–137; Hayner et al., 1988, Cancer Res. 48:368–378). These cells do not arise in nylon screen co-cultures, regardless of the length of the culture or the presence of serum in the medium. In addition, the serum conditioning that has been reported to adversely affect cP450 function in hepatocytes cultured on plastic flasks does not influence cP450 in the present model. The liver cultures disclosed herein are fed with SFM in order to eliminate non-specific protein binding for ELISA assays but this medium lacks sufficient nutrients to maintain the cells for long term. The most obvious deficiency of this SFM is its inability to support stromal cells, which begin to die after ~48 h, an effect which is ameliorated but not completely abrogated by hydrocortisone supplementation.

PGA single fibers arranged into a felt are used in the working examples since it almost entirely degrades by 30 days in situ. (Naughton et al., 1994, Hematol. Rev. 8:37–49). In other studies, constructs containing fiber bundles are found to persist for substantially longer periods. Fibroblastic compartmentalization of these constructs in vivo presents a tangible problem; connective tissue accumulation around the graft site may inhibit the movement of metabolites, thereby limiting the functional life of the graft (Naughton et al., 1992, Somat. Cell Mol. Gen. 18:451–462). The survival and function of grafts of hepatic PC:stromal cell co-cultures on PGA felt at various implantation sites in rats indicate that these constructs can be surgically implanted as tissue equivalents. The generation of hepatic structures such as sinusoids and ductules implies that the cells are deterministic with respect to their formation of these structures; if all cell types that are normally present in a tissue are present in the culture/graft, they will re-establish their 'normal' orientation in vivo. The present invention also discloses the successful graft of liver tissue that is cultured in vitro.

During incubation, the three-dimensional liver cell culture system should be suspended in the nutrient medium. Cultures should be fed with fresh media periodically. Again, care should be taken to prevent cells released from the culture from sticking to the walls of the vessel where they could proliferate and form a confluent monolayer. The release of cells from the three-dimensional culture appears to occur more readily when culturing tissues such as liver or bonemarrow as opposed to structural tissues. As previously explained, should the released cells stick to the culture vessel and form a confluent monolayer, the proliferation of the three-dimensional culture may be "shut down". This can be avoided by removal of released cells during feeding, transfer of the three-dimensional culture to a new vessel, by agitation of the culture to prevent sticking of released cells to the vessel wall, or by the continuous flow of fresh media at a rate sufficient to replenish nutrients in the culture and remove released cells. In any case, the mature released cells could be collected and crypreserved for future use.

Growth factors and regulatory factors need not be added to the media since these types of factors are elaborated by the three-dimensional stromal cells. However, the addition of such factors, or the inoculation of other specialized cells may be used to enhance, alter or modulate proliferation and cell maturation in the cultures. The growth and activity of cells in culture can be affected by a variety of growth factors such as insulin, growth hormone, somatomedins, colony stimulating factors, erythropoietin, epidermal growth factor, hepatic erythropoietic factor (hepatopoietin), and liver-cell growth factor. Other factors which regulate proliferation and/or differentiation include prostaglandins, interleukins, and naturally-occurring chalones.

5.3. USES OF THE THREE-DIMENSIONAL LIVER CULTURE SYSTEM

The three-dimensional liver culture system of the invention can be used in a variety of applications. These include but are not-limited to transplantation or implantation of the cultured cells in vivo; screening cytotoxic compounds, carcinogens, mutagens growth/regulatory factors, pharmaceutical compounds, etc., in vitro; elucidating the mechanism of certain diseases; studying the mechanism by which drugs and/or growth factors operate; diagnosing and monitoring cancer in a patient; gene therapy; and the production of biologically active products, to name but a few.

For transplantation or implantation in vivo, either the PC obtained from the culture or the entire three-dimensional culture could be implanted, depending upon the need. Three-dimensional-tissue culture implants may, according to the invention, be used to replace or augment existing tissue, to introduce new or altered tissue, or to join together biological tissues or structures. For example, three-dimensional liver tissue implants may be used to correct metabolic deficiencies due to single gene defects in neonates such as ornithine transcarbamylase deficiency, or to augment liver function in cirrhosis patients.

The three-dimensional liver cultures may be used In vitro to screen a wide variety of compounds, such as cytotoxic compounds, growth/regulatory factors, pharmaceutical agents, etc. To this end, the cultures are maintained in vitro and exposed to the compound to be tested. The activity of a cytotoxic compound can be measured by its ability to damage or kill cells in culture. This may readily be assessed by vital staining techniques. The effect of growth/regulatory factors may be assessed by analyzing the cellular content of the matrix, e.g., by total cell counts, and differential cell counts. This may be accomplished using standard cytological and/or histological techniques including the use of immunocytochemical techniques employing antibodies that define type-specific cellular antigens. The effect of various drugs on normal cells cultured in the three-dimensional system may be assessed. For example, drugs that affect cholesterol metabolism, by lowering cholesterol production, could be tested on the three-dimensional liver system.

It is well known that a number of compounds fail to act as mutagens in test organisms such as bacteria or fungi, yet cause tumors in experimental animals such as mice. This is due to metabolic activation; i.e., some chemicals are metabolically altered by enzymes in the liver (the P450 oxidase system and hydroxylation systems) or other tissues, creating new compounds that are both mutagenic and carcinogenic. In order to identify such carcinogens, Ames and his co-workers devised a screening assay which involves incubating the chemical compound with liver extracts prior to exposure of the test organism to the metabolic product (Ames et al., 1975, Mut. Res. 31:347–364). While a more sophisticated approach, the Ames assay still lacks sensitivity. By contrast, the three-dimensional liver cultures can be utilized both as the metabolic converters and the "test organism" to determine the mutagenicity or carcinogenicity of the substance being tested.

The three-dimensional cell cultures may also be used to aid in the diagnosis and treatment of malignancies and diseases. For example, a biopsy of liver tissue may be taken from a patient suspected of having a malignancy. If the biopsy cells are cultured in the three-dimensional system of the invention, malignant cells will be clonally expanded during proliferation of the culture. This will increase the chances of detecting a malignancy and, therefore, increase the accuracy of the diagnosis. Hepatitis virus-infected liver cells may be grown in the culture system of the invention. Moreover, the patient's culture could be used in vitro to screen cytotoxic and/or pharmaceutical compounds in order to identify those that are most efficacious; i.e. those that kill the malignant or diseased cells, yet spare the normal cells. These agents could then be used to therapeutically treat the patient.

The three-dimensional culture system of the invention may afford a vehicle for introducing genes and gene products in vivo for use in gene therapies. For example, using recombinant DNA techniques, a gene for which a patient is deficient could be placed under the control of a viral or tissue-specific promoter. The recombinant DNA construct containing the gene could be used to transform or transfect a host cell which is cloned and then clonally expanded in the three-dimensional culture system. The three-dimensional culture which expresses the active gene product, could be implanted into an individual who is deficient for that product.

The use of the three-dimensional culture in gene therapy has a number of advantages. Firstly, since the culture comprises eukaryotic cells, the gene product will be properly expressed and processed in culture to form an active product. Secondly, gene therapy techniques are useful only if the number of transfected cells can be substantially enhanced to be of clinical value, relevance, and utility; the three-dimensional cultures of the invention allow for expansion of the number of transfected cells and amplification (via cell division) of transfected cells.

Preferably, the expression control elements used should allow for the regulated expression of the gene so that the product is synthesized only when needed in vivo. The promoter chosen would depend, in part upon the type of tissue and cells cultured. Cells and tissues which are capable of secreting proteins (e.g., those characterized by abundant rough endoplasmic reticulum and Golgi complex) are preferable. To this end, liver and other glandular tissues could be selected. Liver specific viral promoters, such as hepatitis B virus elements, could be used to introduce foreign genes into liver cells and regulate the expression of such genes. These cells could then be cultured in the three-dimensional system of the invention. Alternatively, a liver-specific promoter such as the albumin promoter could be used. Examples of transcriptional control regions that exhibit tissue specificity which have been described and could be used, include but are not limited to: albumin gene control region which is active in liver (Pinkert et al., 1987, Genes and Devel. 1:268–276); alpha-fetoprotein gene control region which is active in liver (Krumlauf et al., 1985, Mol. Cell. Biol. 5:1639–1648; Hammer et al., 1987, Science 235:53–58); and alpha-1-antitrypsin gene control region which is active in liver (Kelsey et al., 1987, Genes and Devel. 1:161–171).

In a further embodiment of the invention, three-dimensional cultures may be used to facilitate gene transduction. For example, and not by way of limitation, three-dimensional cultures of stroma comprising a recombinant virus expression vector may be used to transfer the recombinant virus into cells brought into contact with the stromal tissue, thereby simulating viral transmission in vivo. The three-dimensional culture system is a more efficient way of accomplishing gene transduction than are current techniques for DNA transfection.

In yet another embodiment of the invention, the three-dimensional culture system could be used in vitro to produce biological products in high yield. For example, a cell which naturally produces large quantities of a particular biological product (e.g., a growth factor, regulatory factor, peptide hormone, antibody, etc.), or a host cell genetically engineered to produce a foreign gene product, could be clonally expanded using the three-dimensional culture system in vitro. If the transformed cell excretes the gene product into the nutrient medium, the product may be readily isolated from the spent or conditioned medium using standard separation techniques (e.g., HPLC, column chromatography, electrophoretic techniques, to name but a few). A "bioreactor" could be devised which would take advantage of the continuous flow method for feeding the three-dimensional cultures in vitro. Essentially, as fresh media is passed through the three-dimensional culture, the gene product will be washed out of the culture along with the cells released from the culture. The gene product could be isolated (e.g., by HPLC column chromatography, electrophoresis, etc.) from the outflow of spent or conditioned media.

Since liver PC grown on three-dimensional stromal tissue exhibit long-term liver specific functions in vitro, they also may be employed as the core component of an extracorporeal liver assist device. Such a device may be used to treat patients with acute or chronic hepatic failure. The liver culture would function in this setting to assist metabolic processes such as the urea cycle and also to synthesize liver proteins.

Various sample embodiments of the invention are described in the sections below. For purposes of description only, and not by way of limitation, the three-dimensional liver culture system of the invention is described based upon rat liver cells. It is expressly understood that the three-dimensional culture system can be used with other liver cells and tissues, including human.

6. EXAMPLE: THREE-DIMENSIONAL LIVER TISSUE CULTURE SYSTEM

6.1 MATERIALS AND METHODS

6.1.1. PERFUSION AND CELL ISOLATION

Male Long-Evans rats (6–9 weeks of age) were anesthetized with 0.3 ml of injectable sodium pentobarbital intraperitoneally and subjected to a series of prograde perfusions through the portal vein using: $Ca^{2+}$-free buffer (500 ml) (Pertoft and Smedsrod, 1987, In: Cell Separation: Methods and Selected Applications, Vol. 4, Academic Press, New York, pp. 1–24), buffer containing $Ca^{2+}$ and 0.05 g/dl type IV collagenase (100 ml)(Sigma Chemical Co, Mo.), and buffer conditioned with 10% fetal bovine serum (FBS)(50 ml). Medium was perfused at a flow rate of 50 ml/min using a Harvard Instruments (MA) peristaltic pump. Hepatocytes were liberated into suspension, filtered through a 185 $\mu$m nylon sieve, pelleted by centrifugation, and resuspended in complete medium.

Hepatic cells were separated into various subpopulations using either a two-step "PERCOLL" gradient centrifugation (Naughton et al., 1991, In: In Vitro Toxicology, Vol. 8, Mechanisms and New Technology, Mary Ann Liebert, Inc., New York) or a pre-formed continuous gradient. Briefly, neat "PERCOLL" stock solution was diluted to 70% (v/v) with 1× Dulbecco's phosphate buffered saline (DPBS). The cell suspension was overlaid and spun at 1200×g for 15 min at 10° C. in an IEC swing bucket centrifuge to remove cellular debris and erythrocytes. The remaining cells were resuspended in DPBS and layered atop a 25%:50% discontinuous "PERCOLL" gradient and centrifuged as in the first step. Alternatively, a 30% "PERCOLL" solution was spun at 30,000×g for 30 min in a Sorvall RCB5 centrifuge with a 20° fixed angle rotor to form a continuous gradient. Suspensions of hepatic cells were overlaid and centrifuged at 200×g for 15 min at 10° C. The densities of the various isolation zones were determined using density marker beads and cytosmear preparations of cells of each zone were stained with Diff-Quik (Baxter, Ill.).

6.1.2. NYLON SCREEN CULTURE 15 mm×60 mm nylon filtration screens (Tetko, N.Y.) were treated with 1.0M acetic acid, washed in distilled water, and soaked in FBS to enhance cellular attachment. These were placed in Tissue Tek slide chambers (Nunc, Inc., Ill.) and inoculated with $10^7$ liver stromal cells that were expanded in monolayer culture for 3–4 passes. Screens were transferred to 25 cm² flasks 18–24 h later. Within 10 days, projections of developing stromal cells extended across 3 to 4 out of every 5 mesh openings. Screen cultures were placed in slide chambers, inoculated with 2-5×10⁶ hepatic PC or acidophilic reserve cells, and transferred to 25 cm² flasks after 18–24 h. Cells were cultured (5% $CO_2$/35°–37° C./>90% humidity) in DMEM conditioned with 6% FBS and 10% equine serum and supplemented with 10 ng/ml glucagon, 10 $\mu$g/ml insulin (Sigma Chem. Co., Mo.), 10 $\mu$g/ml glucose, and $10^{-7}$M hydrocortisone hemisuccinate. Complete medium replacement was performed 4–5 times per week.

6.1.3. ELISA ASSAYS (a) albumin. Medium collected at each feeding was assayed for rat albumin using the enzyme-linked immunosorbent assay (ELISA). Reagents were purchased from Cappel Inc. (NC). 100 $\mu$l of spent medium was added to 96 well plates and stored at 0° C. for 12–14 h. The wells were washed with 0.05% Tween-20 in PBS and non-specific binding sites were blocked with 5.0% bovine serum albumin (BSA)(Miles Inc., Ill.) in PBS. After washing with 0.05% Tween-20, 100 $\mu$l of peroxidase-conjugated sheep anti-rat albumin was added to each well and incubated for 1 hr at 22° C. The wells were washed with 0.05% Tween-20 and incubated for 15 min with O-phenylenediamine substrate. The reaction was stopped and absorbance at 490 rm was measured with a kinetic microplate reader (Molecular Devices Inc., Calif.). Results were calculated from a standard curve constructed using chromatographically-pure rat albumin.

(b) fibrinogen, fibronectin, and transferrin. Because of the lack of suitable species-specific antibodies for these proteins, liver cultures were transferred to serum-free medium (SFM) for 24 h prior to collection of supernatant samples. The SFM formulation of Enat et al (Enat et al., 1984, Proc. Nat. Acad. Sci. USA 81:1411–1415) was modified by supplementing with hydrocortisone hemisuccinate (50 $\mu$g/ml), fungizone (0.5 $\mu$g/ml), penicillin (5 U/ml), and streptomycin (5 $\mu$g/ml). After 24 h in SFM, cultures were returned to complete medium and samples were stored at −20° C. until assayed. SFM was used as a negative control and affinity-purified proteins including rat fibrinogen (Sigma), rat fibronectin (Chemicon), and rat transferrin (Cappel Inc., NC) were diluted from 7.8125 ng/ml to 1 $\mu$g/ml for a standard curve. All supernatant samples were tested undiluted, in quadruplicate. 50 $\mu$l of control, standard or supernatant were added to each well of a 96 well plate and incubated 15 h at 4° C. Wells were blocked with 0.5% BSA in PBS, for 1 h at 37° C. and washed with 0.05% Tween-20 in PBS. 50 $\mu$l of peroxidase-conjugated antibodies such as anti-human fibrinogen, anti-human fibronectin and anti-rat transferrin (The Binding Site, Ltd., CA) were added to each well, incubated for 1 h at 37° C., and washed with PBS/Tween-20. 50 $\mu$l of K-Blue peroxidase substrate (Elisa Technologies, KY) were added to each well. Plates were incubated at ~35° C. for 10 min in the dark, and read on a Dynatech plate reader at 650 nm.

6.1.4. FLOW CYTOMETRY (a) Phenotypic Analysis. Freshly isolated liver cells and cells derived from liver cultures were reacted on ice with 100 $\mu$l mouse monoclonal $IgG_1$ polymorphic antibodies to either rat MHC I or MHC II antigens which were conjugated to fluorescein isothiocyanate (FITC) (Serotec Inc., UK).

Control cells were treated with mouse IgG$_1$-FITC alone. The samples were analyzed using an EPICS C flow cytometer (Coulter Electronics, FL) tuned to a wavelength of 488 nm with the fluorescence gain adjusted to exclude $\geq 98\%$ of the control cells. Windows were established around the various cell populations using the forward light scatter (FLS) vs. side scatter (SS) two parameter histogram and the percentage of positively fluorescent events was determined.

(b) Cytochrome P-450 (cP450) assay. Cells were analyzed for evidence to cP450 enzyme activity by quantifying incremental fluorescein fluorescence in cells accumulating ethoxyfluorescein ethyl ester (EFEE) (Miller, 1983, Anal. Chem. 133:46–57; White et al., 1987, Biochem. J. 247:23–28). EFEE to fluorescein conversion occurs via the specific cleavage of an ether linkage by a polycyclic aromatic hydrocarbon (PAH)-induced cP450 (Miller, A. G., 1983, Anal. Chem. 133:46–57). As with other cP450-catalyzed reactions, EFEE metabolism requires NADPH, and can be inhibited by carbon monoxide or monoclonal antibodies that decrease PAH or benzo(a)pyrene metabolism (Miller, A. G., 1983, Anal. Chem. 133:46–57). At 18 h prior to cP450 assay, cells were induced with 1 nM of a 1 $\mu$M stock solution of the non-fluorescent compound, 2,3,7,8-tetrachlorodibenzo-p-dioxin (TCDD) (Chemical Carcinogen Repository, National Cancer Institute, Kansas City, Mo.) in dimethylsulfoxide (DMSO) (Sigma Chem. Co.). Cultured cells were lifted using a dispase-collagenase mixture, pelleted and resuspended in phosphate buffered saline (PBS) at a density of $\sim 5 \times 10^5$ cells/ml, stored on ice for 1 h, and gradually warmed to 37° C. Cells were incubated with 50 nM EFEE (Molecular Probes, OR) in PBS for 5 min at 37° C. and examined for green fluorescence on a flow cytometer with a 515 nm long-pass filter and tuned to the 488 nm band. Fluorescence resulting from EFEE to fluorescein conversion was gated on various populations of cells based on differences in FLS vs. SS characteristics and was measured once/minute for up to 25 min in samples maintained at 37°C.

(c) Statistical Analysis. Flow cytometry measurements were taken in triplicate on samples sizes of 5,000 (phenotypic analysis) events. EFEE to fluorescein conversion was measured as a function of time with 3,000 to 5,000 events being sampled per min. for up to 20 min. All results are expressed as x±1 sem. Levels of significance (P) were determined using Student's T test. Data were considered significant at the 5% level.

6.1.5. CELL COUNTS/IDENTIFICATION

Total non-adherent and adherent zone cell counts were determined using a Coulter Model ZM cell counter. Differential cell counts were based strictly on the morphology of cells stained using Diff-Quik (Baxter SP, IL). Phagocytosis of colloidal carbon and reaction with FITC-conjugated antibodies to the vW factor VIII segment were used initially to identify Kupffer cells and vascular endothelial cells, respectively.

6.1.6. IMMUNOCHEMISTRY

Specimens were fixed with 10% formalin in PBS, dehydrated in a graded series of ethanols, cleared with Hemo-De (Fisher Scientific, NJ), embedded in paraffin at 56° C., and sectioned at 5 $\mu$m. Sections were cleared in xylene, re-hydrated in a series of ethanols, and predigested with 0.5 mg/ml bovine testicular hyaluronidase in 0.1N sodium acetate-acetic acid buffer at pH=6.0 (Sigma Chem Co., MO). Slides were blocked with a solution of 4% goat serum, 0.1% BSA, and 0.1% Tween-20 in 0.1M NaCl. Polyclonal rabbit primary antibodies to fibronectin, collagen type III, laminin (Telios Pharmaceuticals, CA), transferrin, albumin, or fibrinogen (Cappel Inc., NC) were reacted with the sections for 1–3 h at 22° C., washed in 0.1% Tween-20 in 0.1M NaCl, placed in Tris buffer for 10 min., and labelled with goat anti-rabbit IgG-FITC for 30 min at 22° C. prior to viewing on a Nikon Epifluorescencer microscope. Enzyme digested serial sections also were reacted with monoclonal antibodies to rat cytokeratin 19 (Chemicon International Inc., CA) for 90 min at 37° C., washed, and incubated with sheep anti-mouse IgG-FITC for 30 min. Photographs were obtained using a Nikon Optiphot fluorescence microscope.

6.1.7. IMPLANTATION OF LIVER CO-CULTURES INTO RATS

PGA felt material (10 mm×60 mm×5 mm) (Davis & Geck, CT) was placed into a Tissue Tek slide chamber (Nunc, Inc. MD), inoculated with $\sim 10^7$ liver stromal cells whose numbers were expanded for several passages in monolayer culture, and suspended in liquid medium. The culture was again placed in a slide chamber and a second inoculum of $5 \times 10^6$ PC was applied 7 days later. The co-culture was grown for an additional 2 weeks and then grafted into the omentum, mesentery, at the excision point of a left hepatic lobectomy, or at subcutaneous sites of Long-Evans rats anesthetized with sodium pentobarbital (104 mg/kg body weight). After 21 days in situ, the grafts were excised, fixed in 10% formaldehyde in PBS, and processed for histological evaluation. 7 $\mu$m serial sections through graft and control sites were cleared in Hemo-De (Fisher Scientific, NJ) and rehydrated through a graded series of ethanols (100%, 90%, 70%) to dH$_2$O. Alternate sections were stained with hematoxylin and eosin or processed for immunocytochemistry as described previously.

6.2. RESULTS

6.2.1. LIVER CELL ISOLATION

The various types of hepatic cells, their relative densities, and method of isolation are listed in Table II. Two major cell groups were identified in these preparations:

(a) Parenchymal cells (PC). Three types of PC were observed based on their morphological characteristics:

Type I. these were small (15–20 $\mu$m) mononuclear hepatocytes with deep cytoplasmic basophilia. These were relatively dense, attached poorly to pre-established stromal cells and did not adhere directly to plastic, and did not proliferate in vitro in association with either substratum.

TABLE II

Isolation characteristics of various liver cells*.

| Cell type | Characteristics | Density (gm/ml) | Percentage of Total |
|---|---|---|---|
| PC: | | | |
| mononuclear | 17-22 $\mu$m deeply basophilic cytoplasm; nucleus: vesicular chromatin pattern with 1–2 nucleoli; MHC I negative; MHC II negative | 1.0669 | 35 |

TABLE II-continued

Isolation characteristics of various liver cells*.

| Cell type | Characteristics | Density (gm/ml) | Percentage of Total |
|---|---|---|---|
| binuclear | 20–27 µm basophilic cytoplasm; nucleus: vesicular chromatin pattern with 1 and occasionally 2 nucleoli; Some weakly express MHC I; MHC II negative | 1.0706 | 24 |
| acidophilic | 25–35 µm lightly acidophilic cytoplasm; nucleus: little condensed chromatin with 2–3 large prominent nucleoli; MHC I negative; MHC II negative | 1.0381 | 5 |
| stroma: | | | |
| Kupffer cells | 12–16 µm lightly basophilic cytoplasm with few vacuoles; moderately basophilic; oval nucleus with no obvious chromatin pattern; phagocytose colloidal carbon; most express low density MHC I; MHC II positive | 1.0363 | 8 |
| Endothelial | 11–12 µm lightly basophilic cytoplasm without inclusions; elliptical nucleus without a remarkable chromatin pattern; MHC I positive; MHC 11 positive; vW factor VIII positive | 1.0363 | 15 |
| Adipocytes | 15–18 µm pale, vacuolated cytoplasm; lightly basophilic nucleus | 1.0363 | 3 |
| Fibroblasts | 12–15 µm lightly basophilic cytoplasm without inclusions; moderately basophilic nucleus with 0–1 nucleoli. | 1.0363 | 10 |

*Separations performed at osmolality of 360–370 mOsM

Type II. these were moderately sized (20–30 µm) binuclear cells with 1–2 nucleoli and moderate to deep cytoplasmic basophilia (FIG. 1A). Some of these cells adhered to plastic and some Type I PC attached to them. They proliferated for 2–3 days after plating in monolayer culture and then became mitotically inactive.

Type III. these large (≧35 µm), ghost-like cells (FIG. 1B) were usually binuclear with 2–3 very prominent nucleoli per nucleus, accumulated little or no basic stain in the cytoplasm and displayed buoyant densities similar to hepatic stromal cells although their volume was substantially greater than these cells. These 'acidophilic' PC adhered rapidly and firmly to plastic, had a much higher mitotic activity than other liver cells, and retained this mitotic activity for 10–14 days in monolayer culture. Such large acidophilic cells represent a population of highly mitotic liver reserve cells. Although virtually all of these cells adhered, all gradually detached from the plastic within 2–3 weeks and assumed the appearance of type II cells. In addition, Type I and Type II PC attached to pre-established monolayers of acidophilic cells.

Although some Type I, II, and III PC weakly expressed MHC I antigens, these were not detectable on most PC cells. PC did not express MHC II antigens.

(b) Stromal cells. This population of hepatic cells included fibroblasts, vascular and biliary endothelia, adipocytes, and Kupffer cells that were co-separated by centrifuging freshly prepared cells against a 70% "PERCOLL" gradient in 10× PBS (density=1.09 gm/ml) for 10 min forming a pellet and a central zone. Cells from the central zone were washed and centrifuged on a 25%/50% "PERCOLL" column. Stromal cells were localized in the interface zone (density=1.03625 g/ml). This isolate also contained small numbers of peripheral blood leukocytes. The small size of stromal cells as compared to PC (FIG. 1A) permitted a relatively simple differentiation of these cell types. However, the individual subpopulations of liver stromal cells were less distinct from each other based purely on morphological parameters. Whereas fibroblasts and adipocytes were identified morphologically, Kupffer cells and endothelial cells were differentiated by their ability to phagocytose colloidal carbon or be recognized by a monoclonal antibody to vW factor, respectively. Moderate levels of MHC I antigens were detected on all of these stromal cell subsets; Kupffer cells and endothelia were the only stroma to express MHC II antigens.

6.2.2. CHARACTERIZATION OF SUSPENDED LIVER CELL NYLON CO-CULTURES

When PC were inoculated onto nylon screens containing preestablished stromal cells, they grew in clusters for the first 1–2 weeks of culture (FIG. 2A); patterns of cell growth were increasingly more difficult to discern after this time because of the high cell density of the framework. The screen itself was composed of nylon fibers that were 90 µm in diameter and arranged into a square weave pattern with openings of 140 µm×140 µm. The total volume for cell growth within each of these spaces was ~1.8 m$^3$. The sections shown in FIGS. 2B and 2C depict the field across one of these screen openings. Stromal cells and their processes are the major elements of the field at several hours after the inoculation of the stromal tissue with PC (FIG. 2B). With time the PC eventually filled in most of the available spaces seen in this section. The section of a 52 day old culture (FIG. 2C) shows a screen space that is tightly packed with large, round PC. The process of filling in this framework was generally complete by 4–6 weeks of co-culture.

Although the radiothymidine incorporation data (FIG. 3A) did not discriminate between PC and stromal cells, it was apparent upon comparison with the absolute adherent cell count and differential counts (FIG. 3B) that the nylon screen framework had a fixed capacity for cell growth, i.e. ~10$^7$ for liver cells. Tritiated thymidine incorporation into DNA decreased as the spaces filled in with growing liver cells and the absolute number of cells plateaued. Differential counts of adherent zone cells revealed increases in the numbers of PC as well as stromal cells with time in vitro (FIG. 3B) but the numbers of PC remained higher than stromal cell counts for the duration of the experiment. The PC, which were considerably larger cells occupied most of the area in the cultures. PC in the suspended nylon screen co-cultures displayed a rounded, as compared to the spread/flat morphology that was typical of hepatocyte culture on plastic flasks. These round cells stained positively for albumin using the immunoperoxidase method (FIG. 4A) and for fibrinogen, transferrin, and fibronectin by immunofluorescence. They also stained positively for cytokeratin 19, an epithelial cell marker found on PC (FIG. 4B). By comparison, the thinner stromal cells that interweaved between the PC in these cultures did not express liver-specific proteins but did stain positively for laminin and collagen type III as well as fibronectin (Table III). Co-cultures established with >85% homogeneous populations of acidophilic PC exhibited higher seeding efficiencies and rates of cluster formation than co-cultures inoculated with mixed PC populations but were not superior in terms of functional activity.

TABLE III

Immunofluorescence detection of various antigens in PC and/or matrix of liver co-cultures or sections of adult liver tissue.

| Antigen | Co-Culture | | Tissue | |
|---|---|---|---|---|
| | Cells | Matrix | Cells | Matrix |
| Albumin | +++ | 0 | var | 0 |
| Collagen type III | 0 | + | 0 | + |
| Cytokeratin 19 | +++ | + | ++ | + |
| Fibrinogen | ++ | 0 | ++ | 0 |
| Fibronectin | ++ | +++ | + | ++ |
| Laminin | 0 | ++ | 0 | + |
| Transferrin | ++ | 0 | + | 0 |

0 = no reaction
+ = low fluorescence
+++ = high fluorescence

PC derived from suspended nylon screen co-cultures displayed TCDD-inducible cP450 enzyme activity for up to 56 days as indicated by their ability to transform EFEE to fluorescein (FIGS. 5 A and B). Since the flow cytometer was gated on discrete populations of cells based upon their physical characteristics (FLS vs. SS), the EFEE to fluorescein conversion was quantified at the cellular level and leakage of fluorescein from the cell to the medium did not influence this measurement. Peak EFEE to fluorescein conversion was >2 times higher in the 17, 26, 41, or 58 day co-cultures than in either freshly isolated liver cells or 24 h suspension cultures of these hepatocytes (FIG. 5B). Although peak fluorescence was not contingent upon the age of the co-culture, different rates of EFEE conversion were observed in cultures of different ages. In addition, the EFEE conversion kinetics of TCDD-primed cells varied depending on the concentration of substrate; transformation of EFEE to fluorescein and subsequent egress from the cells was complete by 14 min at EFEE levels of 2.5 $\mu$l/ml and 5 $\mu$l/ml whereas metabolism of 7.5 $\mu$l/ml of EFEE stock solution did not drop to baseline levels until 23 min after addition of substrate to 58 day old cultures. Although cP450 activity was observed in Kupffer cells and in PC of various sizes, moderate to large PC displayed the highest EFEE to fluorescein conversion. Arbitrary conversion units were calculated as the product of the percent positive fluorescence and peak channel number as described by Miller (Miller, 1983, Anal. Chem. 133:46–57). This provided an index of the percentage of cells having cP450 activity and the strength of their activity.

Although the levels of albumin, fibrinogen, transferrin, and free fibronectin in the medium varied, all were present in the culture medium for up to 48 days (FIG. 6 and FIG. 7). Fibrinogen concentration in the culture medium actually increased over time in culture from $\leq$50 ng/ml for the first 20 days of culture to $\geq$150 ng/ml by 28 days, where it remained for the last 3 weeks of the study. Fibronectin levels increased for up to 40 days but dropped by ~75% by 48 days in vitro. A similar pattern was observed for albumin which was present at peak level at 25 days and dropped by ~25% thereafter to a titer that was constant for the remainder of the experiment. In contrast, transferrin synthesis declined steadily for the first 2 weeks of culture to a level of ~1 $\mu$g/ml that was relatively stable over the next 4 weeks in vitro. Cultured PC manifested a diminished expression of class I MHC antigens when compared to freshly isolated hepatic parenchyma (2.6% vs. 4.9%, respectively). In contrast, no MHC class I antigen expression was detectable on stromal cells and MHC class II epitopes on macrophagic cells were substantially lower than on non-cultured cells (3.5% vs. 9.6% respectively).

6.2.3. IMPLANTATION OF LIVER TISSUES IN RATS

Hepatic tissue architecture was reconstructed at most of the graft sites of liver PC:stromal cell co-cultures on PGA felt (FIGS. 8A, B and C). This regenerating tissue contained sinusoids with lining cells that were macrophagic based on their double staining with monoclonal antibodies against MHC II antigens (OX-6) and the ED-1 epitope. Graft site tissues displayed the appearance of regenerating liver in that the sinusoids were somewhat wider than normal liver, the Kupffer cell: PC number ratio was higher, the PC were less basophilic, and mitotic figures were observed routinely (Bucher, 1987,In: The isolated hepatocyte: use in toxicology and xenobiotic biotransformations, Academic Press, New York, pp. 1–19; Naughton et al., 1977, Science 196:301–302; Naughton et al., 1991, Toxicol. In Vitro 5:389–394). Grafts in omental and subcutaneous sites displayed a higher incidence of generation of these liver specific structures than the mesentery, perhap's because of their relatively higher degree of vascularization. However, even when liver PC: stromal cell co-culture grafts failed to develop liver-like architecture (~25% of the time) they still stained positively for the presence of albumin, transferrin, and fibrinogen indicating that the function of synthesizing these proteins does not require patent sinusoidal structures. The liver grafts did not develop at ectopic sites unless partial hepatectomy was performed at the time of grafting.

7. EXAMPLE: GENETICALLY-ENGINEERED LIVER CELL CULTURES

7.1 MATERIALS AND METHODS

7.1.1. VIRUS PRODUCTION

The retroviral vector LNL-SLX$\beta$gal which contained a 3.1-kb $\beta$ galactosidase gene driven by the mouse dihydrofolate reductase promoter was described in Scharfmann et al., 1994 Proc. Natl. Acad. Sci. USA 88:4626–4630, Naughton et al., 1992, Somat. Cell and Mol. Gen. 18:451. Plasmid DNA (10 $\mu$g) was transfected into the ecotropic packaging line $\psi$CRE by calcium phosphate co-precipitation. The cells were grown in DMEM conditioned with 10% FBS. The medium was changed 24 hr later and at 48 hr after transfection, the medium was harvested and used to infect the amphotropic packaging line $\psi$CRIP in the presence of polybrene (8 $\mu$g/ml). Single colonies of infected $\psi$CRIP were isolated after selection with G418 and expanded to confluence. Recombinant retroviruses were harvested, filtered, and used to infect target cells.

7.1.2. INFECTION OF TARGET CELLS

Liver stromal cells and acidophilic PC were isolated by methods that were described, supra, and were employed as target cells. The infection with the retroviral vector LNL-SLX$\beta$gal was performed as follows:

Day 1. 2–5$\times$10$^6$ target cells were incubated (30° C.,>90% humidity) with 10 ml of a suspension of retroviral vector in DMEM conditioned with 10% FBS and supplemented with 8 $\mu$g/ml of Polybrene. After 2.5 hr, the total volume was adjusted to 20 ml with DMEM.

Day 2. All medium was aspirated from the flasks and the cells were incubated with freshly prepared virus suspension as on day 1.

Day 3. All medium was aspirated and replaced with DMEM complete medium.

Days 4–7. All medium was aspirated and replaced with 100–200 μg/ml G418 in DMEM complete medium for 48 hr on day 4 and again on day 6 to negatively select for the infected cells.

Day 8. All medium was aspirated and replaced with DMEM complete medium.

7.1.3. CULTURING OF RETROVIRALLY-INFECTED CELLS

Liver stromal cells that were transduced with the LNL-SLXβgal vector were grown in monolayer culture for 30 days. Acidophilic liver cells that were transfected with the LNL-SLXβgal vector were either cultured for 2–3 weeks in plastic flasks or were inoculated upon a three dimensional framework containing a pre-established growth of normal non-transfected liver stromal cells. The latter were cultured for 30 days. Expression of β galactosidase activity was visualized by the transformation of 5-bromo-4-chloro-3-indoyl β-D-galactoside (X gal) into a blue-colored compound.

7.2. RESULTS

When the liver stromal cells were infected with the virus, they were efficiently transduced with retroviral vectors and expressed β galactosidase activity throughout the 30 day period of observation in vitro. Acidophilic PC were very sensitive to G418 selection. When they were inoculated into plastic flasks after transfection, they grew at a slower rate than usual but became detached from the plastic surfaces as they matured and developed into type I and type II PC. Approximately, 50–60% of these cells expressed β galactosidase after 3 weeks in culture. In addition, transfected acidophilic cells retained their expression of β galactosidase when cultured upon normal hepatic stromal cells on three-dimensional framework for 30 days.

The present invention is not to be limited in scope by the exemplified embodiments, which are intended as illustrations of individual aspects of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method for determining the effect of a drug on liver parenchymal cells in culture, comprising:
   (a) exposing a three-dimensional liver cell culture to the drug, in which the three dimensional cell culture comprises liver parenchymal cells grown on a living stromal tissue prepared in vitro, comprising stromal cells and connective tissue proteins naturally secreted by the stromal cells attached to and substantially enveloping a framework composed of biocompatible, non-living material formed into a three dimensional structure having interstitial spaces bridged by the stromal cells; and
   (b) determining the effect of the drug on the liver parenchymal cells in culture.

2. The method for testing the effect of a drug according to claim 1 in which the stromal cells are fibroblasts.

3. The method for testing the effect of a drug according to claim 1 in which the stromal cells are a combination of fibroblasts and endothelial cells, pericytes, macrophages, monocytes, leukocytes, plasma cells, mast cells or adipocytes.

4. The method for testing the effect of a drug according to claim 1 in which the framework is composed of a biodegradable material.

5. The method for testing the effect of a drug according to claim 4 in which the biodegradable material is cotton, polyglycolic acid, cat gut sutures, cellulose, gelatin, or dextran.

6. The method for testing the effect of a drug according to claim 1 in which the framework is composed of a non-biodegradable material.

7. The method for testing the effect of a drug according to claim 6 in which the non-biodegradable material is a polyamide, a polyester, a polystyrene, a polypropylene, a polyacrylate, a polyvinyl, a polycarbonate, a polytetrafluorethylene, or a nitrocellulose compound.

8. The method for testing the effect of a drug according to claims 4, 5, 6 or 7 in which the framework is pre-coated with collagen.

9. The method according to claim 8 in which the framework is a mesh.

10. The method according to claims 1, 2, 3, 4, 5, 6, or 7 in which the framework is a mesh.

11. A method for studying the mechanism of a disease or condition in a patient, which disease or condition has a detectable effect on liver parenchymal cells in culture comprising:
   (a) inoculating liver parenchymal cells from a sample obtained from the patient onto a living stromal tissue prepared in vitro, comprising stromal cells and connective tissue proteins naturally secreted by the stromal cells attached to and substantially enveloping a framework composed of a biocompatible, non-living material formed into a three-dimensional structure having interstitial spaces bridged by the stromal cells;
   (b) culturing the inoculated living stromal tissue in a nutrient medium so that the inoculated liver parenchymal cells proliferate in culture; and
   (c) analyzing the proliferated liver parenchymal cells in culture for markers of the disease or condition.

12. The method for studying disease mechanisms according to claim 11 in which the stromal cells are fibroblasts.

13. The method for studying disease mechanisms according to claim 11 in which the stromal cells are a combination of fibroblasts and endothelial cells, pericytes, macrophages, monocytes, leukocytes, plasma cells, mast cells or adipocytes.

14. The method for studying disease mechanisms according to claim 11 in which the framework is composed of a biodegradable material.

15. The method for studying disease mechanisms according to claim 14 in which the biodegradable material is cotton, polyglycolic acid, cat gut sutures, cellulose, gelatin, or dextran.

16. The method for studying disease mechanisms according to claim 11 in which the framework is composed of a non-biodegradable material.

17. The method for studying disease mechanisms according to claim 11 in which the non-biodegradable material is a polyamide, a polyester, a polystyrene, a polypropylene, a polyacrylate, a polyvinyl, a polycarbonate, a polytetrafluorethylene, or a nitrocellulose compound.

18. The method for studying disease mechanisms according to claims 14, 15, 16, or 17 in which the framework is pre-coated with collagen.

19. The method according to claim 18 in which the framework is a mesh.

20. The method according to claims 11, 12, 13, 14, 15, 16 or 17 in which the framework is a mesh.

* * * * *